(12) United States Patent
Benkovic et al.

(10) Patent No.: US 7,846,710 B2
(45) Date of Patent: *Dec. 7, 2010

(54) CELL COMPRISING AN INTEIN FOR THE PRODUCTION OF A CYCLIC PEPTIDE

(75) Inventors: Stephen J. Benkovic, State College, PA (US); Charles P. Scott, State College, PA (US); Ernesto V. Abel-Santos, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 469 days.

This patent is subject to a terminal disclaimer.

(21) Appl. No.: 11/670,112

(22) Filed: Feb. 1, 2007

(65) Prior Publication Data

US 2007/0207502 A1 Sep. 6, 2007

Related U.S. Application Data

(63) Continuation of application No. 09/868,469, filed as application No. PCT/US99/30162 on Dec. 18, 1999, now Pat. No. 7,354,756.

(60) Provisional application No. 60/112,723, filed on Dec. 18, 1998, provisional application No. 60/158,077, filed on Oct. 7, 1999.

(51) Int. Cl.
| | |
|---|---|
| *C12P 21/06* | (2006.01) |
| *C12N 9/00* | (2006.01) |
| *C12N 9/14* | (2006.01) |
| *C12N 1/20* | (2006.01) |
| *C12N 15/00* | (2006.01) |
| *C07H 21/04* | (2006.01) |

(52) U.S. Cl. ............... 435/252.3; 435/69.1; 435/183; 435/195; 435/320.1; 536/23.2

(58) Field of Classification Search ................ None
See application file for complete search history.

(56) References Cited

U.S. PATENT DOCUMENTS 5,643,758 A 7/1997 Guan et al.

OTHER PUBLICATIONS

Iwai et al. "Cyclic Green Fluorescent Protein Produced in Vivo Using an Artificially Split Pl-Pful Intein From *Pyrococcus furiosus*", The Journal of Biological Chemistry, (2001), vol. 276, No. 19, pp. 16548-16554.

Kinsella et al. "Retrovirarlly Delivered Random Cyclic Peptide Libraries Yield Inhibitors of Interleukin-4 Signaling in Human B Cells", The Journal of Biological Chemistry, (2002), vol. 277, No. 40, pp. 37512-37518.

Scott et al. "Structural requirements for the biosynthesis of backbone cyclic peptide libraries", Chemistry & Biology, (2001), vol. 8, pp. 801-815.

Derbyshire et al. "Genetic definition of a protein-splicing domain: Functional mini-inteins support structure predictions and a model for intein evolution", Proc. Natl. Acad. Sci. USA, (1997), vol. 94, pp. 11466-11471, (1997).

Scott et al. "Production of cyclic peptides and proteins in vivo", PNAS, (1999), vol. 96, No. 24, pp. 13638-13643.

Williams et al. "In Vivo Protein Cyclization Promoted by a Circularly Permuted *Synechocystis* sp. PCC6803 DNAB Mini-intein", The Journal of Biological Chemistry, (2002), vol. 277, No. 10, pp. 7790-7798.

*Primary Examiner*—Christian L Fronda
(74) *Attorney, Agent, or Firm*—Novak Druce + Quigg LLP; J. Rodman Steele, Jr.; Amy A. Dobbelaere

(57) ABSTRACT

Methods of producing cyclic peptides and splicing intermediates of peptides in a looped conformation are disclosed. The methods utilize the trans-splicing ability of split inteins to catalyze cyclization of peptides from a precursor peptide having a target peptide interposed between two portions of a split intein. The interaction of the two portions of the split intein creates a catalytically-active intein and also forces the target peptide into a loop configuration that stabilizes the ester isomer of the amino acid at the junction between one of the intein portions and the target peptide. A heteroatom from the other intein portion then reacts with the ester to form a cyclic ester intermediate. The active intein catalyzes the formation of an aminosuccinimide that liberates a cyclized form of the target peptide, which spontaneously rearranges to form the thermodynamically favored backbone cyclic peptide product. Also disclosed are nucleic acid molecules, polypeptides, methods for making cyclic peptides, methods of making libraries, and methods of screening peptides.

12 Claims, 30 Drawing Sheets

CELL COMPRISING AN INTEIN FOR THE PRODUCTION OF A CYCLIC PEPTIDE

CROSS REFERENCE TO RELATED APPLICATIONS

This application is a continuation of U.S. patent application Ser. No. 09/868,469, filed Sep. 24, 2001; now U.S. Pat. No. 7,354,756 which is a §371 Application of International Application No. PCT/US99/30162, filed Dec. 18, 1999; which claims priority to U.S. Provisional Application No. 60/112,723 filed Dec. 18, 1998 and U.S. Provisional Application No. 60/158,077, filed Oct. 7, 1999, entitled "Production of Cyclic Peptides and Proteins In Vivo", all of which are incorporated herein by reference.

STATEMENT AS TO FEDERALLY SPONSORED RESEARCH

This invention was made with Government support under grant number GM19891, awarded by the National Institutes of Health. The Government has certain rights in the invention.

FIELD OF THE INVENTION

The invention relates to the field of biochemistry. More particularly, the invention relates to cyclic peptides, methods for the making cyclic peptides, and methods of screening cyclic peptides for particular characteristics.

BACKGROUND OF THE INVENTION

Small linear peptides are useful for investigating various physiological phenomena because they exhibit a wide range of biological activities and can be easily synthesized in almost infinitely variable sequences utilizing conventional techniques in solid phase synthesis and combinatorial chemistry. These qualities also make small linear peptides especially useful for identifying and developing new drugs. For example, large libraries of myriad different small linear peptides can be prepared synthetically and then screened for a particular characteristic in various biological assays. E.g., Scott, J. K. and G. P. Smith, Science 249:386, 1990; Devlin, J. J., et al., Science 24:404, 1990; Furka, A. et al., Int. J. Pept. Protein Res. 37:487, 1991; Lam, K. S., et al., Nature 354:82, 1991. Those peptides within the library that exhibit the particular characteristic can then be isolated as candidates for further study. Microsequencing or other chemical analyses can then be used to characterize selected peptides by, for example, amino acid sequence. Despite these advantages, only a handful of small linear peptides have been developed into widely-used pharmaceutical drugs. One reason for this is that small linear peptides are usually cleared from the body too rapidly to be of therapeutic value.

Ring closure, or cyclization, can reduce the rate at which peptides are degraded in vivo and therefore dramatically improve their pharmocokinetic properties. The majority of cyclic peptides of known therapeutic value have been identified after isolation from natural sources (e.g., calcitonins, oxytocin, and vasopressin). Unfortunately, the pool of naturally-existing cyclic peptides that can be screened for a particular biological activity is inherently limited. And, moreover, the onerous steps required to isolate and purify cyclic peptides from natural sources render such screens costly and impractical. Thus, synthetic methods for producing large numbers of different peptides of infinitely variable amino acid sequences would greatly facilitate identifying particular cyclic peptides as candidates for new drugs.

Various methods for producing cyclic peptides have been described. For example, chemical reaction protocols, such as those described in U.S. Pat. Nos. 4,033,940 and 4,102,877, have been devised to produce circularized peptides. In other techniques, biological and chemical methods are combined to produce cyclic peptides. These latter methods involve first expressing linear precursors of cyclic peptides in cells (e.g., bacteria) to produce linear precursors of cyclic peptides and then adding of an exogenous agent such as a protease or a nucleophilic reagent to chemically convert these linear precursors into cyclic peptides. See, e.g., Camerero, J. A., and Muir, T. W., J. Am. Chem. Society. 121:5597 (1999); Wu, H. et al, Proc. Natl. Acad. Sci. USA, 95:9226 (1998).

Once produced, cyclic peptides can be screened for pharmacological activity. For example, a library containing large numbers of different cyclic peptides can be prepared and then screened for a particular characteristic, such as the ability to bind a specific target ligand. The library is mixed with the target ligand, and those members of the library that bind to the target ligand can be isolated and identified by amino acid sequencing. Similarly, libraries of cyclic peptides can be added to assays for a specific biological activity. Those cyclic peptides which modulate the biological activity can then be isolated and identified by sequencing.

Unfortunately, because the step of identifying the active peptides can be difficult, these screening assays can prove laborious and time-consuming. For instance, screening assays usually mandate a reverse-mapping step because the actual amount of cyclic peptide that binds a target ligand or modulates a biological activity is usually so minute that it cannot be sequenced directly. To avoid this problem, a map indicating the physical location of the various cyclic peptides comprising a library can be made. Aliquots of cyclic peptides from the different locations are then transferred to corresponding locations within the screening assay; and those areas in the assay that exhibit the screened-for activity (e.g., binding or modulation of biological activity) are then mapped back to their corresponding location in the library. The cyclic peptides in that area of the library can then be isolated and sequenced. Difficulties arising from the need for spatial resolution and the limitations imposed by sample handling limit the number of candidate peptides that can be screened in any given period of time.

The number of peptides that can be screened in an assay can be dramatically increased by using cells that express the peptides. For example, bacteria engineered to express a library of linear peptides can be added to a screening assay, and those bacteria that express the screened for characteristic can be picked directly from the assay. The picked bacteria can then be reproduced to large numbers such that the selected linear peptides can made in large quantities to facilitate their identification (e.g., by sequencing) and production. Making and screening small linear peptide libraries in vivo has, however, proven to be troublesome because small linear peptides are rapidly degraded by normal cellular metabolic processes. Cyclization of the peptides can circumvent this problem by rendering the peptides stable within a cell.

Despite this, heretofore, intracellular production of large libraries of cyclic peptides has not been feasible because general, easy-to-perform methods for cyclizing peptides in vivo have not been available. For example, a known method of producing cyclic peptides in vivo utilizes non-ribosomal peptide synthetase (NRPS) complexes (Cane et al, Science 282:63, 1998). Such NRSP complexes are, however, neither facile to work with nor generally useful for the production of more than a single cyclic peptide at a time. Moreover, unlike ribosomal peptide synthesis where the linear sequence of monomers (amino acids) is dictated by the linear sequence of bases in the nucleic acid molecule encoding it, the linear sequence of monomers in a peptide made by the NRPS method is dictated by the subunit organization of the NRPS complex. Changing the sequence of a cyclic peptide made by NRPS entails cloning the subunit(s) which incorporate the desired monomers and introducing the subunit(s) into host cells already harboring all of the other necessary subunits. Making a library using this technique would require introducing combinations (both in composition and order) of NRPS subunits to host cells and devising a method for ensuring that the subunits assemble into the correct supramolecular structures.

SUMMARY OF THE INVENTION

A general method for the in vivo production and screening of cyclic peptide libraries has been discovered. In this method, a nucleic acid molecule is constructed such that a nucleotide sequence encoding the peptide to be cyclized is flanked on one end with a nucleotide sequence encoding the carboxy-terminal portion of a split (or trans) intein (C-intein or $I_C$) and on its other end with a nucleotide sequence encoding the amino-terminal portion of a split intein (N-intein or $I_N$). Expression of the construct within a host system such as a bacterium or eukaryotic cell results in the production of a fusion protein. The two split intein components (i.e., $I_c$ and $I_n$) of the fusion protein then assemble to form an active enzyme that splices the amino and carboxy termini together to generate a backbone cyclic peptide. The chemical reaction is depicted below.

Mechanism of Intein Mediated Cyclization

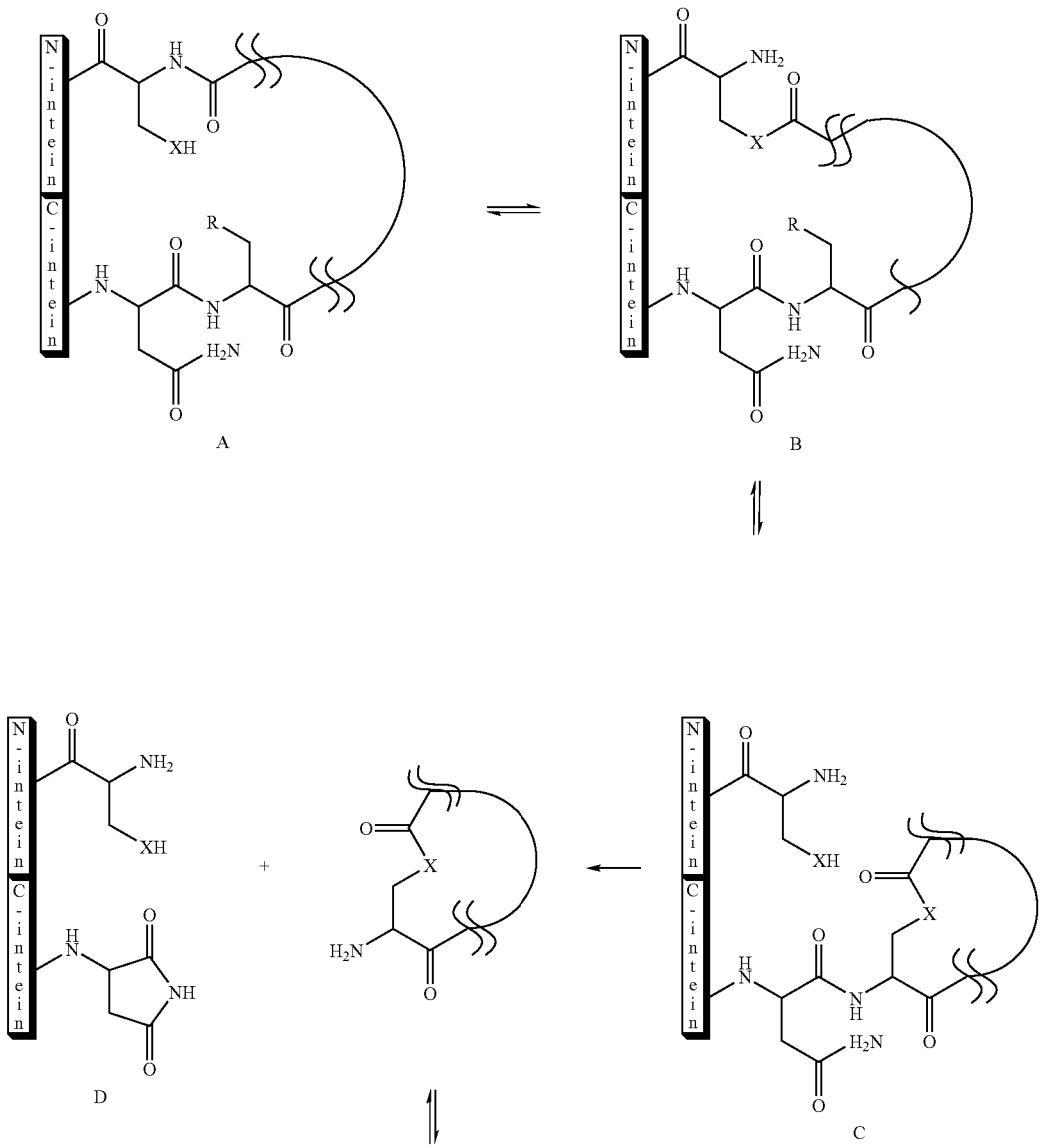

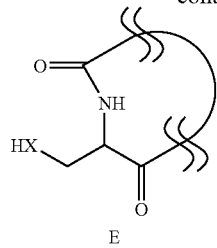

Formation of the active intein from the amino and carboxy-terminal fragments stabilizes the ester isomer of an amino acid at the junction between the N-interin and the peptide to be cyclized (in B above X=S or O). When R=XH, the heteroatom from the C-intein is poised to attack the ester and generate a cyclic ester intermediate (C). Intein-catalyzed amino-succinimide formation (D) liberates the cyclic peptide (in the lactone form), which spontaneously rearranges to form the thermodynamically favored backbone (lactam form) cyclic peptide product (E). This method can be adapted to facilitate the selection or screening of cyclic peptides with predetermined characteristics.

Accordingly the invention features a non-naturally occurring nucleic acid molecule encoding a polypeptide having a first portion of a split intein, a second portion of a split intein, and a target peptide interposed between the first portion of a split intein and the second portion of a split intein. Expression of the nucleic acid molecule in a host system produces a polypeptide that spontaneously splices in the host system to yield a cyclized form of the target peptide, or a splicing intermediate of a cyclized form of the target peptide such as an active intein intermediate, a thioester intermediate, or a lariat intermediate.

Both the first portion of a split intein and the second portion of a split intein can be derived from a naturally-occurring split intein such as Ssp DnaE. In other variations, one or both of split intein portions can be derived from non-naturally occurring split inteins such as those derived from RecA, DnaB, Psp Pol-I, and Pfu inteins.

In another aspect, the invention features a non-naturally occurring nucleic acid molecule encoding a polypeptide having a first portion of a split intein, a second portion of a split intein, a third portion of a split intein, and fourth portion of a split intein. This molecule can have a first target peptide is interposed between the first portion of a split intein and the second portion of a split intein, and a second target peptide is interposed between the third portion of a split intein and the fourth portion of a split intein. The first portion of a split intein can be complementary to the third portion of a split intein but not complementary to the second portion of a split intein, and the second portion of a split intein can be complementary to the fourth portion of a split intein but not complementary to the third portion of a split intein.

Also within the invention is an expression vector comprising a nucleic acid molecule within the invention. Expression of the vector in a host system produces a polypeptide that spontaneously splices in the host system to yield a cyclic peptide or a splicing intermediate. The expression vector of the invention can also contain a regulatory sequence that facilitates expression of the polypeptide in the host system. The nucleic acid molecule of the vector can include a nucleotide sequence that encodes a peptide that facilitates screening of the cyclized form of the target peptide for a particular characteristic and/or a nucleotide sequence that encodes a peptide that facilitates purifying the cyclized form of the target peptide from the host system. The expression vector can also be inducible.

In another aspect, the invention features an expression vector encoding a polypeptide having a target peptide that has a first end fused to a first portion of a split intein and a second end fused to a second portion of a split intein. Expression vectors of the invention can be a plasmid, a bacteriophage, a virus, a linear nucleic acid molecule, or other type of vector.

The invention additionally features a substantially pure polypeptide having a first portion of a split intein, an second portion of a split intein, and a target peptide interposed between the first portion of a split intein and the second portion of a split intein. The polypeptide can be one that spontaneously splices in the host system to yield a cyclized form of the target peptide, or it can be a splicing intermediate.

Also within the invention is a host system harboring a nucleic acid molecule of the invention. The host system can be a prokaryote such as a bacterium, an archaebacterium, a eukaryote such as a yeast or a mammalian cell, a plant cell, an in vitro transcription/translation system, or a cell lysate.

In another aspect, the invention features a method for making a peptide molecule. This method includes the steps of: providing an isolated nucleic acid molecule of the invention; providing a host system; introducing the isolated nucleic acid molecule into the host system; and expressing the isolated nucleic acid molecule. In one variation, the step of expressing the isolated nucleic acid molecule results in production of a polypeptide that spontaneously splices in the host system to yield the cyclized form of the target peptide. This method can also feature the step of purifying the cyclized form of the target peptide from the host system.

In another variation of this method, the step of expressing the isolated nucleic acid molecule results in production of a splicing intermediate of a cyclized form of the target peptide. This method can also feature the step of purifying the splicing intermediate of a cyclized form of the target peptide from the host system. Yet another variation of this method, includes the step of forming the cyclic peptide from the splicing intermediate.

In another aspect of this method, the target peptide is produced in a cyclized form in the host system in the absence of an exogenously-added agent such as a protease or a thiol.

Another aspect of the invention is a method of preparing a library of peptide molecules. This method involves the steps of providing a plurality of nucleic acid molecules encoding a plurality of target peptides having heterogenous amino acid sequences; incorporating each of the plurality of nucleic acid molecules into an expression vector to form a plurality of expression vectors, and expressing the expression vectors in the host system. The plurality of nucleic acid molecules is interposed between a nucleic acid molecule encoding a first portion of a split intein and a nucleic acid molecule encoding an second portion of a split intein in each of the formed expression vectors such that expression of the expression vectors in a host system results in the production of a plurality of peptide molecules such as polypeptides that spontaneously splice in the host system to yield cyclized forms of the target peptides, or splicing intermediates of cyclized forms of the target peptides And in yet another aspect, the invention includes a method of screening a peptide molecule for a predetermined characteristic. This method includes the steps of: providing a nucleic acid molecule that encodes a polypeptide comprising a first portion of a split intein, a second portion of a split intein, and a target peptide interposed between the first portion of a split intein and the second portion of a split intein; providing the host system; introducing the isolated nucleic acid molecule in the host system; placing the host system under conditions that cause the peptide molecule to be produced; and testing the peptide molecule for the predetermined characteristic. Expression of the nucleic acid molecule in a host system produces either a cyclized form of the target peptide resulting from spontaneously splicing of the polypeptide in the host system, or a splicing intermediate of a cyclized form of the target peptide.

In one variation of this method, the predetermined characteristic includes the ability to specifically bind a target molecule, and the step of testing the peptide molecule for the predetermined characteristic includes the steps of (a) contacting the peptide molecule to the target molecule and (b) determining whether the peptide molecule binds to the target molecule. In another variation, the predetermined characteristic is the ability to modulate a biochemical reaction, and the step of testing the peptide molecule for the predetermined characteristic comprises the steps of (a) contacting the peptide molecule to a system containing the biochemical reaction and (b) determining whether the peptide molecule modulates the biochemical reaction. The step of determining whether the peptide molecule binds to a target molecule or modulates a biochemical reaction can measured by observing a color change, a fluorescent signal, by analyzing the cell cycle or the reproduction of an organism.

The target molecule in these methods can be a cell-associated molecule such as a membrane-associated molecule or an intracellular molecule (e.g., a nuclear molecule or one or more organelles such as mitochondria, lysosomes, endoplasmic reticula, chloroplasts, golgi, and periplasm). It can also be an extracellular molecule.

The biochemical reaction can be a cell associated-process such as an intracellular metabolic event, a membrane-associated event, a nuclear event. It can also be an extracellular reaction.

In these methods, the step of testing the peptide molecule for the predetermined characteristic can be performed using a hybrid system, and/or the step of immobilizing the peptide molecule on a solid phase support.

The invention also features a method for purifying a cyclic peptide from a mixture. This method includes the steps of: providing a mixture containing a splicing intermediate conjugated with an affinity tag; mixing the conjugated splicing intermediate with a solid phase support having a ligand thereon that specifically binds the affinity tag such that the support becomes specifically bound with the splicing intermediate; washing the support to remove non-specifically bound matter from the support; adding to the support a reagent that makes a cyclic peptide from the splicing intermediate; and eluting the cyclic peptide from the support.

In a variation of the foregoing, the invention also includes a method for purifying a cyclic peptide from a mixture that includes the steps of: providing a mixture containing a splicing intermediate conjugated with an affinity tag; mixing the conjugated splicing intermediate with a solid phase support having a ligand thereon that specifically binds the affinity tag such that the support becomes specifically bound with the splicing intermediate;

washing the support to remove non-specifically bound matter from the support; eluting the splicing intermediate from the support; and adding a reagent the eluted splicing intermediate that make a cyclic peptide from the splicing intermediate.

Additionally, included in the invention is method for purifying a target molecule that binds a splicing intermediate from a mixture. This method includes the steps of: providing a solid phase support having the splicing intermediate specifically bound thereon; contacting the support with the target molecule in the mixture; washing the support to remove non-specifically bound matter from the support; and eluting the target molecule from the support.

As used herein, the phrase "non-naturally occurring" means being directly or indirectly made or caused to be made through human action. Thus, a non-naturally occurring nucleic acid molecule is one that has been produced through human manipulation, and not natural evolutionary processes.

By the phrase "nucleic acid molecule" is meant any chain of two or more nucleotides bonded in sequence. For example, a nucleic acid molecule can be a DNA or an RNA.

As used herein, the term "peptide" means a chain of two or more amino acids bonded in sequence, and includes polypeptides and proteins. By "polypeptide" is meant a polymer comprised of two or more peptides, regardless of length or post-translational modification. By "protein" is meant any chain of amino acids and includes peptides, polypeptides, proteins, and modified proteins such as glycoproteins, lipoproteins, phosphoproteins, metalloproteins, and the like.

A "linear peptide" is a peptide that is not in a circular form, and generally has both a carboxy-terminal amino acid with a free carboxy-terminus and an amino-terminal amino acid with a free amino terminus.

In comparison, a "cyclic peptide" is a peptide that has been "cyclized." The term "cyclic" means having constituent atoms forming a ring. When referring to a peptide, the term "cyclize" means to make the peptide into a cyclic or "cyclized" form. Thus, for example, a linear peptide is "cyclized" when its free amino-terminus is covalently bonded to its free carboxy-terminus (i.e., in a head to tail format) such that no free carboxy- or amino-terminus remains in the peptide.

As used herein, a "splicing intermediate" is a polypeptide generated during the intein-mediated cyclization reaction illustrated above prior to the formation of the liberated cyclic peptide product. Splicing intermediates include "active-intein intermediates" (i.e., those with a chemical structure similar to the polypeptide labeled "A" in the above illustration), "thioester intermediates" (i.e., those with a chemical structure similar to the polypeptide labeled "B" in the above illustration), and "lariat intermediates" (i.e., those with a chemical structure similar to the polypeptide labeled "C" in the above illustration).

By the phrase "target peptide" is meant a peptide to be cyclized or displayed in a splicing intermediate. For example, a peptide interposed between a carboxy-terminal portion of a split intein and an amino-terminal portion of a split intein in a precursor protein would be a target peptide, if the peptide becomes cyclized upon splicing of the precursor protein or becomes a part of a splicing intermediate upon processing (e.g., folding) of the precursor protein.

As used herein, the word "intein" means a naturally-occurring or artificially-constructed polypeptide sequence embedded within a precursor protein that can catalyze a splicing reaction during post-translation processing of the protein. A list of known inteins is published at http://www.neb.com/inteins.html. A "split intein" is an intein that has two or more separate components not fused to one another.

As used herein, the word "interposed " means placed in between. Thus, in a polypeptide having a first peptide interposed between a second and a third peptide, the chain of amino acids making up the first peptide is physically located in between the chain of amino acids making up the second peptide and the chain of amino acids making up the third peptide.

A plurality of peptides having "heterogenous amino acid sequences" means that the plurality of peptides is composed of at least two, but generally a large number of, different peptides of disparate amino acid sequence.

As used herein, the phrase "host system" refers to any medium or vehicle in which a nucleic acid molecule can be transcribed, replicated, and/or translated; and/or any medium or vehicle in which a polypeptide can be spliced or otherwise post-translationally processed.

As used herein, the word "spontaneously" means the action described occurs without the addition of an exogenous substance. For example, a precursor polypeptide within a host system spontaneously splices in the host system to yield a cyclic peptide when nothing is added to the host system other than the precursor polypeptide or a nucleic acid molecule encoding the precursor polypeptide. In comparison, a precursor polypeptide within a host system does not spontaneously splice in the host system if an agent extraneous to the host system is required to generate the cyclic peptide.

As used herein, the term "splice" or "splices" means to excise a central portion of the polypeptide to form two or more smaller polypeptide molecules. In some cases, splicing also includes the step of fusing together two or more of the smaller polypeptides to form a new polypeptide.

As used herein, the word "derived" means directly or indirectly obtained from, isolated from, purified from, descended from, or otherwise arising from.

As used herein, the phrase "expression vector" means a vehicle that facilitates transcription and/or translation of a nucleic acid molecule in a host system. An expression vector is "inducible" when adding an exogenous substance to a host system containing the expression vector causes the vector to be expressed (e.g., causes a nucleic acid molecule within the vector to be transcribed into mRNA).

By the phrase "expression of" a nucleic acid is meant that the nucleic acid is transcribed and/or translated into a polypeptide and/or replicated.

As used herein, the phrase "regulatory sequence" means a nucleotide sequence which modulates expression (e.g., transcription) of a nucleic acid molecule. For example, promoters and enhancers are regulatory sequences.

By the term "fused" is meant covalently bonded to. For example, a first peptide is fused to a second peptide when the two peptides are covalently bonded to each other (e.g., via a peptide bond).

As used herein an "isolated" or "substantially pure" substance is one that has been separated from components which naturally accompany it. Typically, a polypeptide is substantially pure when it is at least 50% (e.g., 60%, 70%, 80%, 90%, 95%, and 99%) by weight free from the other proteins and naturally-occurring organic molecules with which it is naturally associated.

A "progenitor DNA" is particular deoxyribonucleic acid from which mutations are made or based upon.

By the phrase "target molecule" is meant any molecule used to determine the binding or functional characteristics of another molecule.

Herein, "bind" or "binds" means that one molecule recognizes and adheres to another molecule in a sample, but does not substantially recognize or adhere to other molecules in the sample. One molecule "specifically binds" another molecule if it has a binding affinity greater than about $10^5$ to $10^6$ liters/mole for the other molecule.

A "cell-associated process" is one that takes place within a cell or in the near vicinity of the cell.

A "membrane-associated event" is a cell-associated process that takes place on the plasma membrane of a cell.

A "nuclear event" is a cell-associated process that takes place in the nucleus of a cell.

In comparison to a cell-associated event, an "extracellular reaction" is one that does not take place within a cell.

By the phrase "hybrid system" is meant two-hybrid systems, reverse two-hybrid systems, one-hybrid systems, split-hybrid systems, small molecule hybrid systems and all like systems for identifying interactions between peptides and other molecules (e.g., proteins and nucleic acid molecules). For a review of exemplary hybrid systems, see Vidal and Legrain, Nucleic Acids Res. 27:919, 1999.

Unless otherwise defined, all technical terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions will control. In addition, the particular embodiments discussed below are illustrative only and not intended to be limiting.

Other features and advantages of the invention will be apparent from the following detailed description, and from the claims.

BRIEF DESCRIPTION OF THE DRAWINGS

The invention is pointed out with particularity in the appended claims. The above and further advantages of this invention may be better understood by referring to the following description taken in conjunction with the accompanying drawings, in which:

DETAILED DESCRIPTION

The trans-splicing ability of split inteins has been exploited to develop a general method of producing cyclic peptides and splicing intermediates displaying peptides in a looped conformation. In this method, a target peptide is interposed between two portions of a split intein in a precursor polypeptide. In an appropriate host system, the two portions of the split intein physically come together to form an active intein in a conformation that also forces the target peptide into a loop configuration. In this configuration, the ester isomer of the amino acid at the junction between one of the intein portions (e.g., $I_N$) and the target peptide is stabilized such that heteroatom from the other portion of the intein (e.g., $I_C$) can then react with the ester to form a cyclic ester intermediate. The active intein then catalyzes the formation of an aminosuccinimide that liberates a cyclized form of the target peptide (i.e., a lactone form), which then spontaneously rearranges to form the thermodynamically favored backbone cyclic peptide product (i.e., the lactam form). By arresting the reaction at given points before liberation of the cyclic peptide, splicing intermediates bearing the target peptide in a loop configuration can be produced. To produce such peptides, nucleic acid molecules encoding a polypeptide having the target peptide sequence interposed between the two intein portions can be constructed. Introduction of these constructs into an expression vector provides a method for producing the polypeptide in a host system, where the polypeptide can be spliced into a cyclic peptide or a splicing intermediate. Using this method, several different cyclic peptides or splicing intermediates can be prepared to generate a library of cyclized or partially-cyclized peptides that can be screened for particular characteristics.

Figure 1:
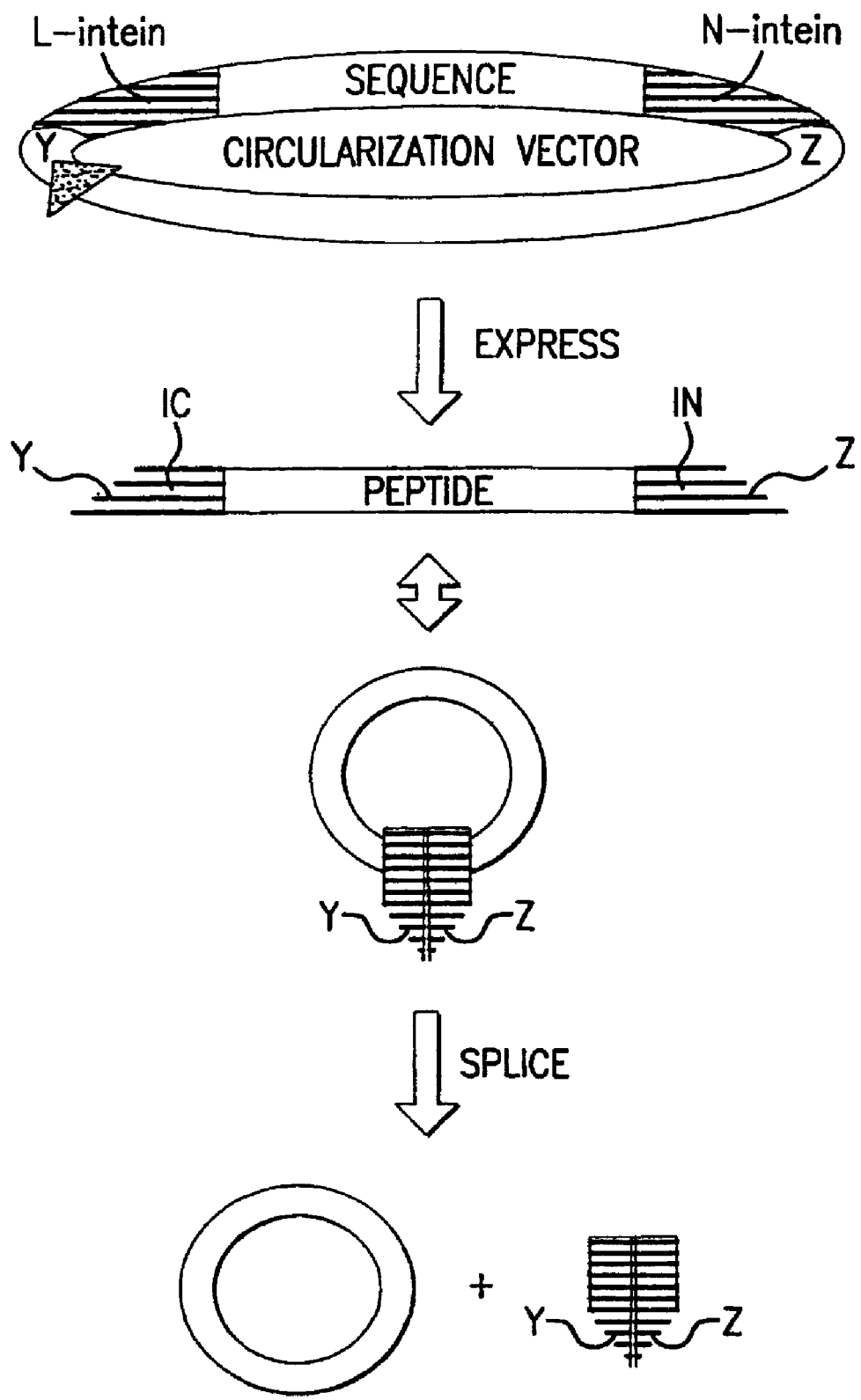
FIG. 1 is a schematic illustration of an overview of a general cyclization reaction within the invention.
Figure 2:
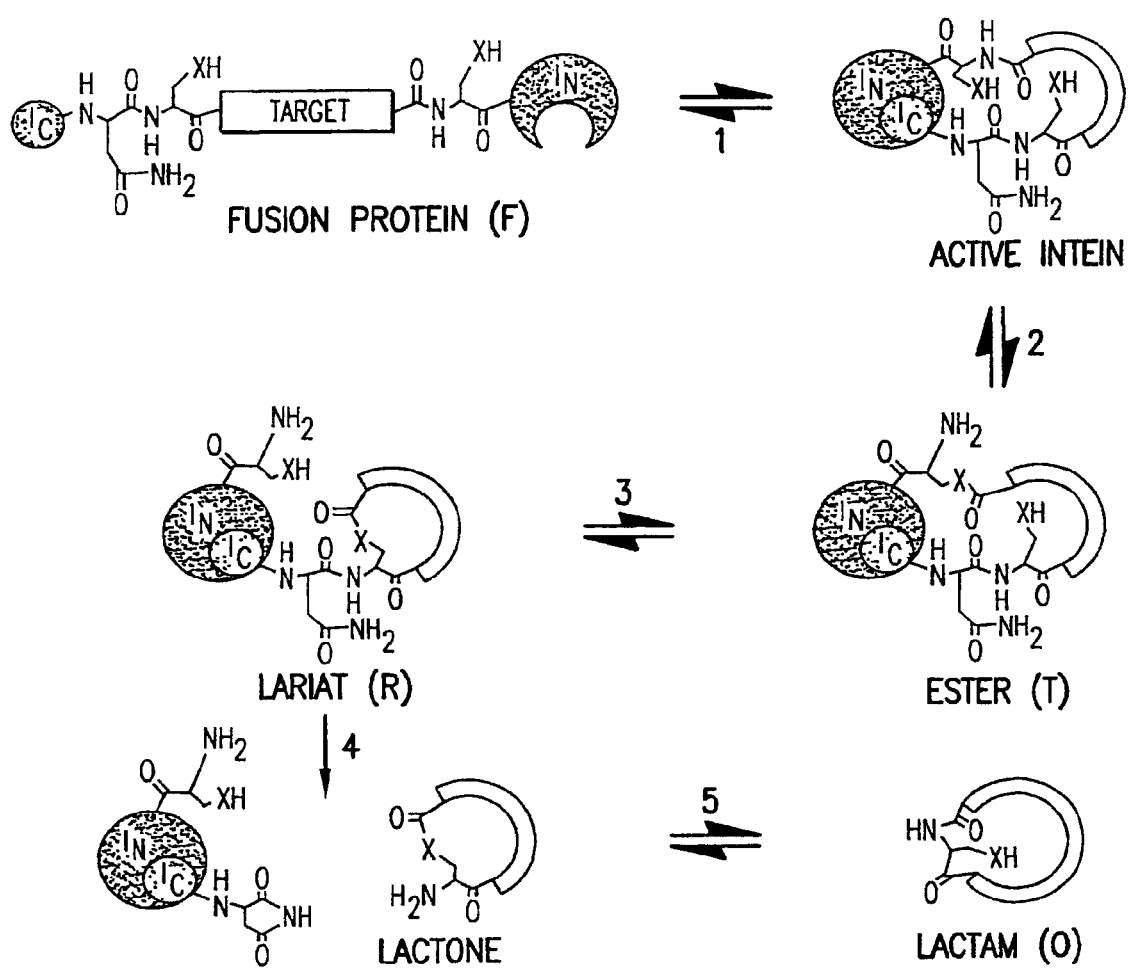
FIG. 2 is a schematic illustration of a series of chemical reaction steps that occur in a peptide cyclization method of the invention.
Figure 3A:
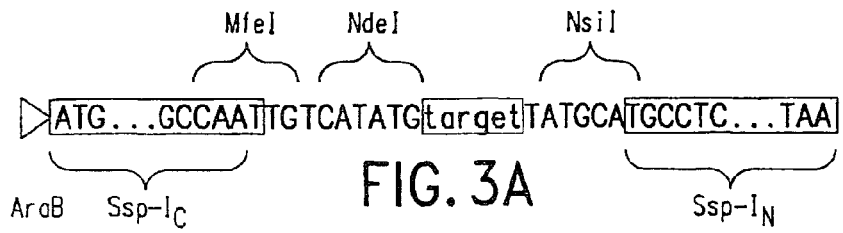
FIG. 3 is a genetic map of (a) plasmid pARCP, (b) plasmid pARCP-DHFR, (c) plasmid pARCPAH-DHFR, (d) a modified vector having a cysteine (TGY) or serine (TCN) codon generated by cloning into the MfeI site (N represents any nucleobase, S represents C or G and Y represents pyrimidines), (e) plasmid pARCP-p, and (f) plasmid pARCBD-p.
Figure 3B:
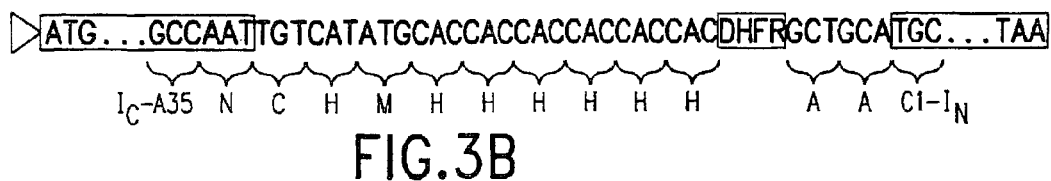
Figure 3C:
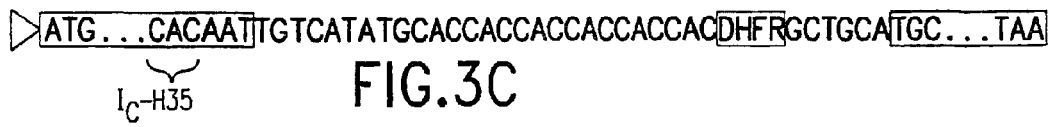
Figure 3D:
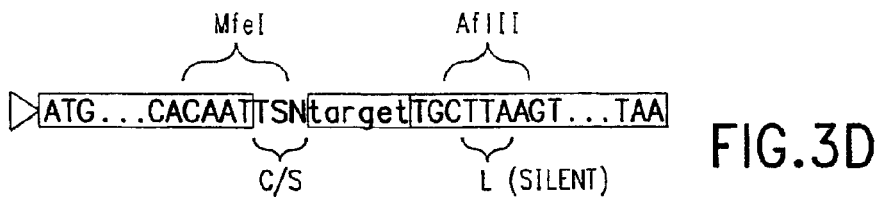
Figure 3E:
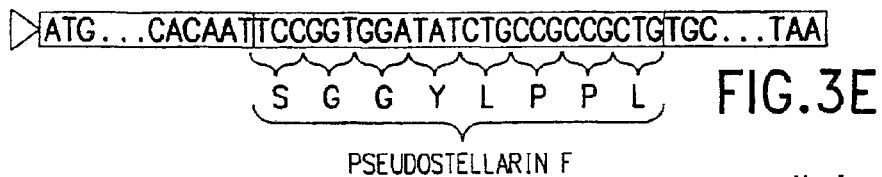
Figure 3F:
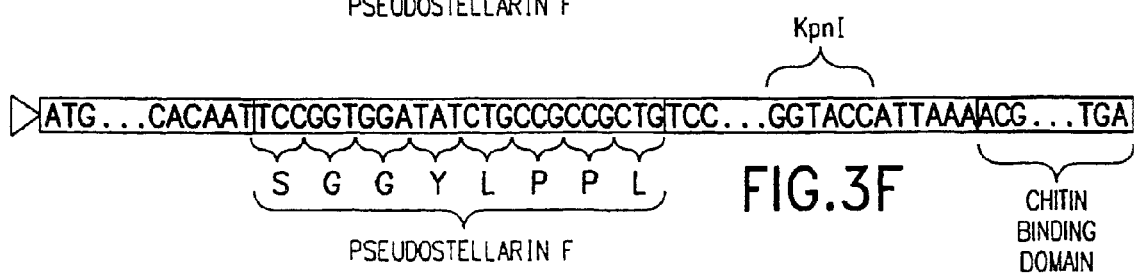

Referring to FIG. 1, an overview of an embodiment of the invention includes a method of making a cyclic peptide from a nucleic acid molecule. In this method, a nucleic acid molecule is prepared so that its nucleotide sequence encodes a polypeptide having in consecutive order a first portion of a split intein (e.g., $I_C$), a peptide to be cyclized (i.e., a target peptide), and a second portion of a split intein (e.g., $I_N$). The nucleic acid molecule can be incorporated into an expression vector to facilitate its expression in a host system where the nucleic acid can be transcribed and translated into a precursor polypeptide having the peptide to be cyclized interposed between the two split intein portions. By the steps described above, the two portions of the split intein come together and place the precursor peptide in a conformation that sets off chemical reactions that ultimately yield a cyclic peptide (see FIG. 2).

Nucleic Acid Molecules

Nucleic acids molecules within the invention include those that encode a polypeptide having a first portion of a split intein, a second portion of a split intein, and a target peptide positioned in between the first portion of a split intein and the second portion of a split intein. In one embodiment of the invention, expression of the nucleic acid molecule in a host system results in a polypeptide that spontaneously splices in the host system to yield a cyclized form of the target peptide. In another embodiment of the invention, expression of the nucleic acid molecule in a host system results in a polypeptide that is a splicing intermediate of a cyclized form of the target peptide. The nucleic acids of the invention can be prepared according to the methods described herein, and can also be prepared using the guidance provided herein in conjunction with methods for preparing and manipulating nucleic acid molecules generally known in the art (See, e.g., Ausubel et al, eds., *Current Protocols in Molecular Biology*, New York: John Wiley & Sons, 1997; Sambrook et al., *Molecular Cloning: A laboratory Manual* ($2^{nd}$ Edition), Cold Spring Harbor Press, 1989). For example, a nucleic acid molecule within the invention can be made by separately preparing a polynucleotide encoding the first portion of a split intein, a polynucleotide encoding the second portion of a split intein, and a polynucleotide encoding the target peptide. The three polynucleotides can be ligated together to form a nucleic acid molecule that encodes a polypeptide having the target peptide interposed between the first portion of a split intein and the second portion of a split intein.

Nucleic Acids Encoding Inteins

Nucleotide sequences that encode the first portion of a split intein and the second portion of a split intein of the nucleic acid molecules within the invention can be derived from known inteins. A fairly comprehensive and descriptive list of such inteins is published by New England Biolabs at http//www.neb.com/inteins/int_reg.html. Any of these known inteins can be used as long as they are compatible with invention.

Nucleotide sequences that encode either naturally-occurring or artificially-produced split inteins can be used to generate the intein portions of nucleic acid molecules within the invention. Naturally-occurring split inteins are expressed in nature as two separate components that bind one another to form one active splicing agent. The nucleic acid molecules encoding these naturally-occurring components can thus be used in the invention. One example of a naturally-occurring split intein that may be used is Ssp DnaE (Wu et al, Proc. Natl. Acad. Sci. USA 95:9226,1998).

Inteins that are not split in their natural state (i.e., those that exist as one continuous chain of amino acids) can be artificially split using known techniques. For example, two or more nucleic acid molecules encoding different portions of such inteins can be made so that their expression yields two or more artificially split intein components. See, e.g., Evans et al, J. Biol. Chem. 274:18359, 1999; Mills et al, Proc. Natl. Acad. Sci. USA 95:3543, 1998. The nucleic acids that encode such non-naturally occurring intein components (portions) can be used in the invention. Those nucleic acid molecules that encode non-naturally occurring split intein portions which efficiently interact on the same precursor polypeptide to yield cyclic peptides or splicing intermediates are preferred. Examples of non-naturally occurring split inteins from which such nucleic acid molecules can be derived include Psp Pol-I (Southworth, M. W., et al, The EMBO J. 17:918, 1998), *Mycobacterium tuberculosis* RecA intein, (Lew, B. M., et al, J. Biol. Chem. 273:15887, 1998; Shingledecker, K., et al, Gene 207:187, 1998; Mills, K. V., et al, Proc. Natl. Acad. Sci. USA 95:3543, 1998), Ssp DnaB/Mxe GyrA (Evans, T. C. et al, J. Biol. Chem. 274:18359, 1999), and Pfu (Otomo et al, Biochemistry 38:16040, 1999; Yamazaki et al, J. Am. Chem. Soc.120:5591, 1998).

Nucleic Acids Encoding Target Peptides or Peptides Displayed in Splicing Intermediates Numerous methods of making nucleic acids encoding peptides of a known or random sequence are known in art. For example, polynucleotides having a predetermined or a random sequence can be prepared chemically by solid phase synthesis using commercially available equipment and reagents. Polymerase chain reaction can also be used to prepare polynucleotides of known or random sequences. See, e.g., Ausubel et al, supra. As another example, restriction endonucleases can be used to enzymatically digest a larger nucleic acid molecule or even whole chromosomal DNA into a plurality of smaller polynucleotide fragments that can be used to prepare nucleic acid molecules of the invention.

Polynucleotides that encode peptide sequences to be cyclized are preferably prepared so that one terminus of the polynucleotide encodes an asparagine, serine, cysteine, or threonine residue to facilitate the cyclization reaction. For the same reason polynucleotides that encode peptide sequences for production of splicing intermediates are preferably prepared so that the terminus encodes an amino acid other than an asparagine, serine, cysteine, or threonine residue so that the cyclization reaction is prevented.

Ligation Polynucleotides Encoding Intein Portions and Target Peptides or Peptides Displayed in Splicing Intermediates Once generated, conventional methods can be used to ligate nucleic acid molecules encoding intein portions to a nucleic acid molecule encoding a target peptide (or peptide within a splicing intermediate) to form a larger nucleic acid molecule encoding a polypeptide having the first intein portion-target peptide-second intein portion order. See, e.g., Ausubel et al, supra.

Nucleic Acid Molecules that Encode Multiple Split Inteins and Multiple Peptides

Using techniques similar to those described above, one skilled in the art could also prepare nucleic acid constructs that encode more than one set of two portions of a split intein interposed with peptides. For example, the invention includes nucleic acids molecules encoding a precursor polypeptide molecules comprised of N polypeptides (N=an integer greater than or equal to 1) and having N target peptides interposed between 2N intein portions such that any target peptide i (i=an integer greater than 1 representing the position of an target peptide in the precursor polypeptide) is interposed between intein portion 2i−1 and 2i (e.g. target peptide 1 is between intein portion 1 & 2, target peptide 2 is between intein portions 3 & 4 etc.). As long as intein portions 2i−1 and 2i are not complementary (i.e. able to physically interact to catalyze a splicing event), target peptide i can not cyclize. If, however, intein portion 2i is complementary with intein portion 2i+1 and intein portion 2N is complementary with intein portion 1, the entire ensemble of N polypeptides can perform N-1 trans splices (between 2 polypeptides) and 1 cis splice (ligating the two ends together) to give rise to a product wherein 1-N target peptides are covalently attached to one another in a cyclic peptide/protein (e.g., intein portions 2 & 3 trans-splice target peptides 1 & 2; intein portions four & five trans-splice target peptides 2 & 3; intein portions 2N-2 & 2N-1 trans-splice target peptides N-1 & N; and intein portions N & 1 cis-splice to close the cyclic product containing the N target sequences). The order of trans/cis splicing events is irrelevant. The slowest splicing species (whether it is the complementary intein portion 2N&1, 2&3 or 80&81) will by default perform the cis-splice.

Thus, nucleic acid constructs can be made that express two or more polypeptides each composed of a target peptide interposed between two portions of a split intein where the intein components are not complementary (i.e., do not derive from the same intein or otherwise cooperate to catalyze any of the cyclization reactions). In such constructs, no one polypeptide could be cyclized unless it was expressed in the presence of a second polypeptide having the appropriate complementary intein component. Constructs of such nucleic acids within the invention could encode only one polypeptide per construct or more than one polypeptide per construct (e.g., a bi-functional plasmid).

Expression Vectors

The expression vectors of the present invention can be prepared by inserting polynucleotides encoding a target peptide into any suitable expression vector that can facilitate expression of the polynucleotide in a host system. Such suitable vectors include plasmids, bacteriophages, and viral vectors. A large number of these are known in the art, and many are commercially available or obtainable from the scientific community. Those of skill in the art can select suitable vectors for use in a particular application based upon, e.g., the type of host system selected (e.g., in vitro systems, prokaryotic cells such as bacteria, and eukaryotic cells such as yeast or mammalian cells) and the expression conditions selected.

Expression vectors within the invention can include a stretch of nucleotides that encodes a target polypeptide and a stretch of nucleotides that operate as a regulatory domain that modulates or controls expression (e.g., transcription) of nucleotide sequences within the vector. For example, the regulatory domain can be a promoter or an enhancer.

Expression vectors within the invention can include nucleotide sequences that encode a peptide that facilitates screening of the cyclized form of the target peptide or splicing intermediate for a particular characteristic (e.g., an affinity tag such as a chitin-binding domain or a biotin tag; a colored or light-emitting label; a radioactive tag; etc. ), or purifying the cyclized form of the target peptide or splicing intermediate from a host system (e.g., an affinity tag such as a chitin-binding domain, a biotin tag, a colored or light-emitting label; a radioactive tag; etc.).

In preferred embodiments, the expression vectors within the invention are produced with restriction sites both between and within the nucleic acid sequences that encode the split intein portions to enable the cloning of a wide variety of cyclization targets or splicing intermediates. In some embodiments, an expression vector of the invention can be an inducible expression vector, such as an arabinose inducible vector. Such vectors can be utilized to control expression of cyclization precursors or splicing intermediates within a host system. Other vectors can be selected for use in the invention based on their compatibility with known bacterial expression strains and hybrid systems. See, e.g., Zhang et al, Curr. Biol. 9:417, 1999; Pellitier et al, Nat. Biotechnol. 17:683, 1999; Karimova et al, Proc. Natl. Acad. Sci. USA 95:5752, 1998; Dmitrova et al, Mol. Gen. Genet., 257:205, 1998; Xu et al, Proc. Natl. Acad. Sci. USA 96:151, 1999; Rossi et al, Proc. Natl. Acad. Sci. USA 94:8405, 1997.

Polypeptides

Polypeptides within the invention include any that can be produced by expression of a nucleic acid of the invention. For example, a substantially pure precursor polypeptide that has a target peptide (or a peptide to be displayed by a splicing intermediate) interposed between the first portion of a split intein and the second portion of a split intein is included in the invention. In some embodiments of the precursor polypeptide, the target peptide may be directly fused to the first and second intein portions. The precursor polypeptide spontaneously splices in the host system to yield a cyclized form of the target peptide (or a splicing intermediate displaying a peptide).

Cyclized forms of target peptides and splicing inter-mediates displaying peptides are also within the invention. Preferably, these are produced by splicing of a precursor polypeptide of the invention. The cyclized forms of target peptides can be of any amino acid sequence that can be cyclized by the methods of the invention The splicing intermediate can be an active intein intermediate, a thioester intermediate, or a lariat intermediate, and can display a peptide of any compatible amino acid sequence.

Host Systems

Hosts systems that may be used in the invention include any systems that support transcription, translation, and/or replication of a nucleic acid molecule of the invention; or that support post-translational modification (e.g., splicing) of a polypeptide or protein of the invention. Numerous such hosts systems are known. For example, in the invention, especially when it is desired to avoid artifacts or interference caused by living host systems, the host system can take the form of an in vitro transcription/translation system. Such systems can be fabricated in the laboratory according to published techniques or can be commercially purchased. For instance, STP2-T7 (cat. No. 69950-3) and STP-SP6 (cat. No. 69997-3) are available from Novagen (Madison, Wis.). Promega (Madison, Wis.) also sells such systems (e.g., cat. Nos. L1170, L2080, L4600, L4610, L4130, L4140, L1130, L1020, and L1030), as does Stratagene (La Jolla, Calif.) which markets a system branded IN VITRO EXPRESS (cat. No. 200360). Non-living host systems for use in the invention can also be derived from a living organism. For example, a cell lysate such as a reticulocyte lysate can be used in some applications.

Host systems can also take the form of living organisms. Living organisms are preferred for host systems because they can usually be reproduced in numerous copies thereby providing a continuous, readily-expandable, and easily-manipulated source of selected nucleic acid molecules. Living organisms that can be used as host systems within the invention include prokaryotes such as bacteria (e.g., *Escherichia coli*) and eukaryotes such as yeasts and mammalian (e.g., human, murine, bovine, ovine, porcine, etc.) cells. Archaebacteria, plant cells, and any other organism suitable for use with the methods of the invention can also function as the host system.

The particular host system best suited for a particular application will vary depending on the many different factors. One of skill in the art, however, should be able to select a suitable host system for a particular application based on known applications of the different host systems. For example, where large scale production of a cyclic peptide is desired, a bacterial host or an insect host would be suitable. As another example, where it is desired to analyze the interaction of human cell components, using a human cell as the host system would likely be more appropriate than using a bacterial system.

Method of Making a Polypeptide, Cyclic Peptide, or a Splicing Intermediate

The polypeptides of the invention can be prepared by conventional methods of producing polypeptides of a known amino acid sequence. For example, polypeptides within the invention can be made by solid phase synthesis using commercially available equipment and reagents. Known, in vitro methods of producing cyclic peptides can also be used to produce cyclic peptides. In many cases, however, the polypeptides of the invention are preferably produced by expressing nucleic acid molecules encoding them in a host system. For example, nucleic acid molecules within the invention can be incorporated into an expression vector and then introduced into a host system. The host system can then be placed under conditions that cause the vector to be expressed, resulting in the formation of a precursor peptide and subsequently a cyclized form of the target peptide or a splicing intermediate displaying the peptide.

A preferred method for making a cyclic peptide or a splicing intermediate includes the steps of: (a) providing an isolated nucleic acid molecule that encodes a polypeptide having a target peptide interposed between the first portion of a split intein and the second portion of a split intein; (b) providing a host system; (c) introducing the isolated nucleic acid molecule into the host system; and (d) expressing the isolated nucleic acid molecule. Expression of the nucleic acid molecule in the host system produces the peptide molecule in the form of a splicing intermediate of a cyclized form of the target peptide, or a polypeptide that spontaneously splices to yield a cyclized form of the target peptide.

In preferred embodiments of this method, production of the polypeptides, cyclic peptides, or splicing intermediates takes place in vivo (e.g., with a living host system) and in the absence of any exogenously-added agent, such as an agent to catalyze cyclization of a peptide (e.g., a protease or a thiol).

Production of polypeptides, cyclic peptides, or splicing intermediates can be monitored monitored using standard techniques for characterizing proteins. See, e.g., Sambrook et al, supra. Exemplary techniques that can be used include conventional chromatography, HPLC, FPLC and the like; electrophoresis such as sodium dodecyl sulfate polyacrylamide gel electrophoresis (SDS/PAGE), 2-dimensional gel electrophoresis; electromagnetic radiation-based-spectroscopy, mass spectroscopy; analysis of enzymatic digestion products; thermostability assays; etc.

Purification of Polypeptides, Cyclic Peptides, or a Splicing Intermediates of the Invention Conventional methods of purifying proteins can be adapted to purify the polypeptides, cyclic peptides, and splicing intermediates of the invention. The invention also includes a preferred method for purifying a cyclic peptide from a mixture. In this method, an affinity tag is attached to the cyclic peptide to aid in its purification. This method includes the steps of: (a) providing a mixture containing a cyclic peptide conjugated with an affinity tag; (b) mixing the conjugated cyclic peptide with a solid phase support having a ligand thereon that specifically binds the affinity tag so that the support becomes specifically bound with the cyclic peptide; (c) washing the support to remove non-specifically bound matter; and (d) eluting the cyclic peptide from the support.

In this method, the affinity tag can any molecule that can bind a ligand on a solid phase support. For example, the affinity tag can be a chitin-binding domain where the ligand is chitin (see examples section below) or it can be a biotin tag where the ligand is streptavidin. Many other affinity tag-ligand pairs are known and can be used in the invention. Because the affinity tag specifically binds the ligand on the solid phase support, the cyclic peptides (with the attached affinity tag) will specifically bind the support. The support can then be washed with a buffer (e.g. a high salt, acid or alkaline buffer) that removes matter within the mixture that is non-specifically bound to the support. The affinity-tagged cyclic peptide can then be eluted from the solid phase support using a buffer containing a substance that separates the tag from the ligand (e.g., a competitive inhibitor such as excess unconjugated affinity tag; or a denaturing agent), or an enzyme or chemical reactant that cleaves the cyclic peptide from the affinity tag.

In an analogous manner, splicing intermediates rather than cyclic peptides can be purified. Cyclic peptides can also be purified from a mixture using splicing intermediates. For example, a method for purifying a cyclic peptide from a mixture includes the steps of: (a) providing a mixture containing a splicing intermediate conjugated with an affinity tag; (b) mixing the conjugated splicing intermediate with a solid phase support having a ligand thereon that specifically binds the affinity tag such that the support becomes specifically bound with the splicing intermediate; (c) washing the support to remove non-specifically bound matter; (d) adding to the support a reagent that makes a cyclic peptide from the splicing intermediate; and (e) eluting the cyclic peptide from the support. In a variation of the foregoing, steps (d) and (e) are reversed so that step (d) is eluting the splicing intermediate from the support and step (e) is adding to the eluted splicing intermediate a reagent that makes a cyclic peptide from the splicing intermediate. Reagents that may be added to make a cyclic peptide from a splicing intermediate include thiols, proteases, and other substances which can catalyze cyclization of the splicing intermediate.

As a specific example, by fusing $I_C$ to an affinity tag and removing the essential asparagine residue (see d in FIG. 3), a cyclic ester can be immobilized on an affinity column. The resulting cyclic peptide column can be used for the affinity purification of the cyclic peptide itself. A wide range of proteolytic methods can be employed to liberate the cyclic ester from the affinity tag and $I_C$ depending upon the sequence of the cyclic peptide product.

Figure 8A:
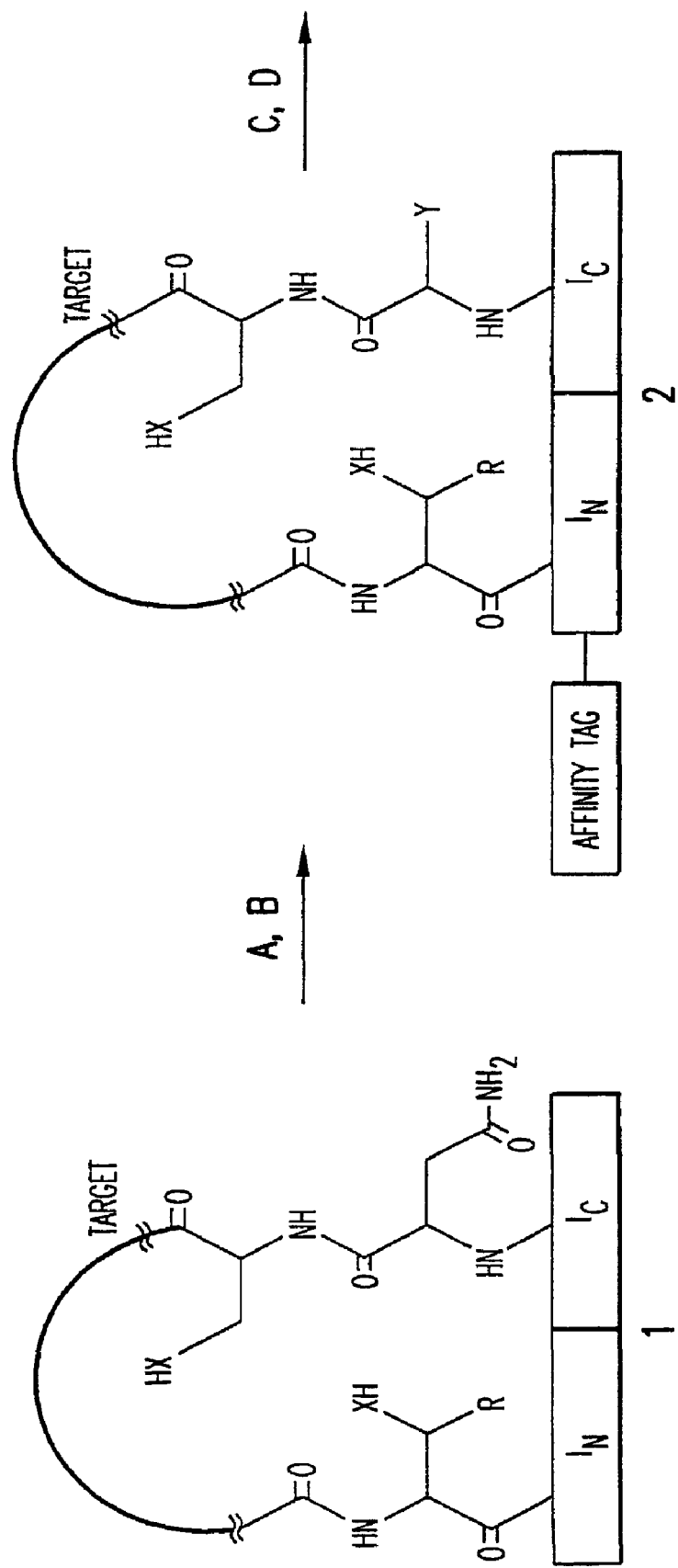
FIG. 8 is a schematic illustration of a method for purifying cyclic peptides within the invention.
Figure 8B:
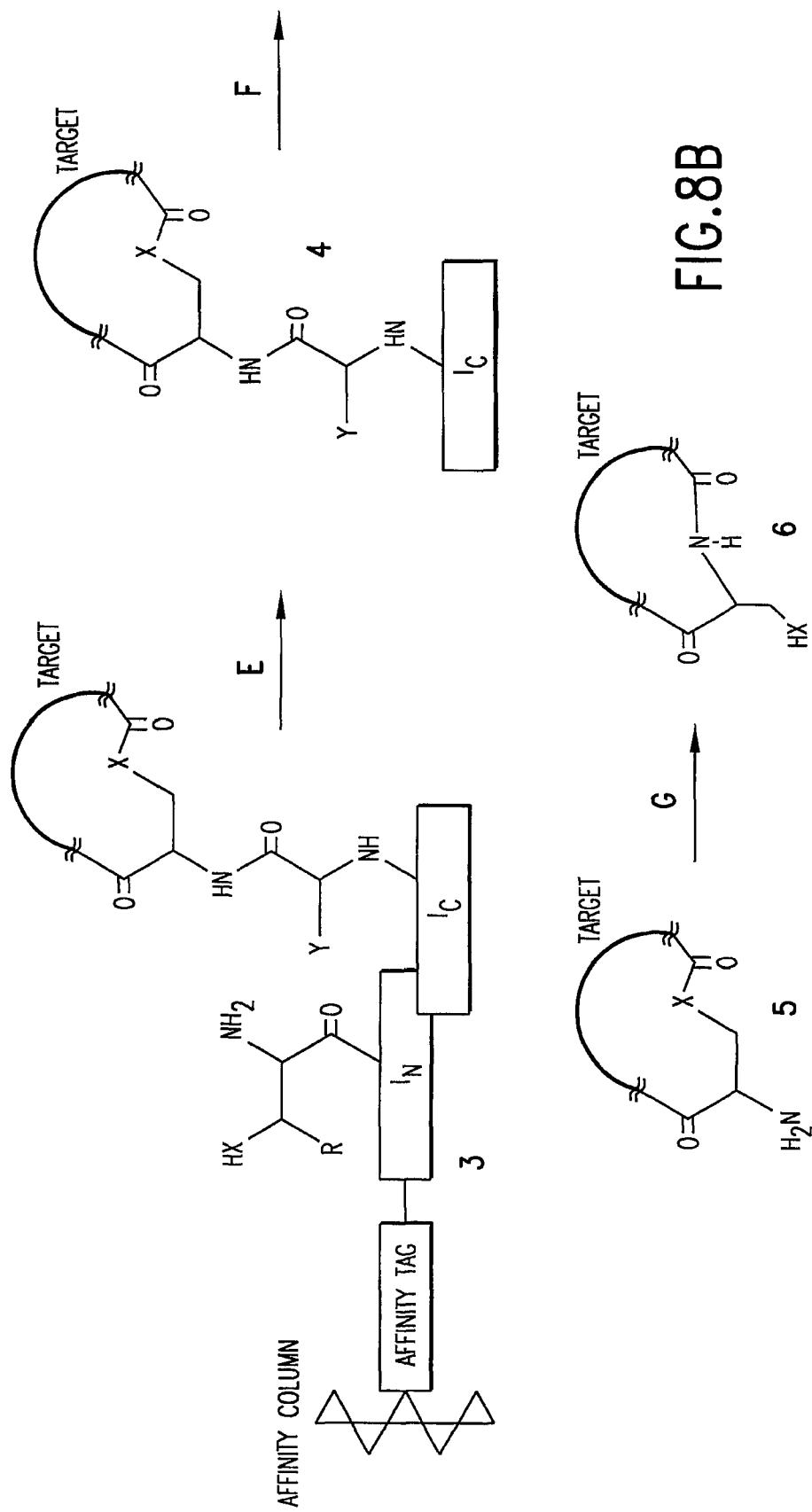
Figure 9A:
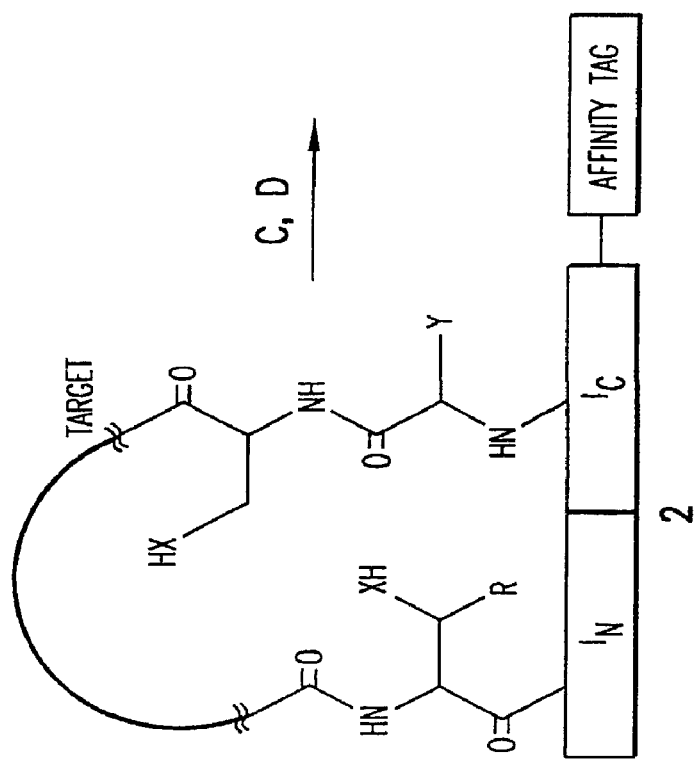
FIG. 9 is a schematic illustration of another method for purifying cyclic peptides within the invention.
Figure 9A:
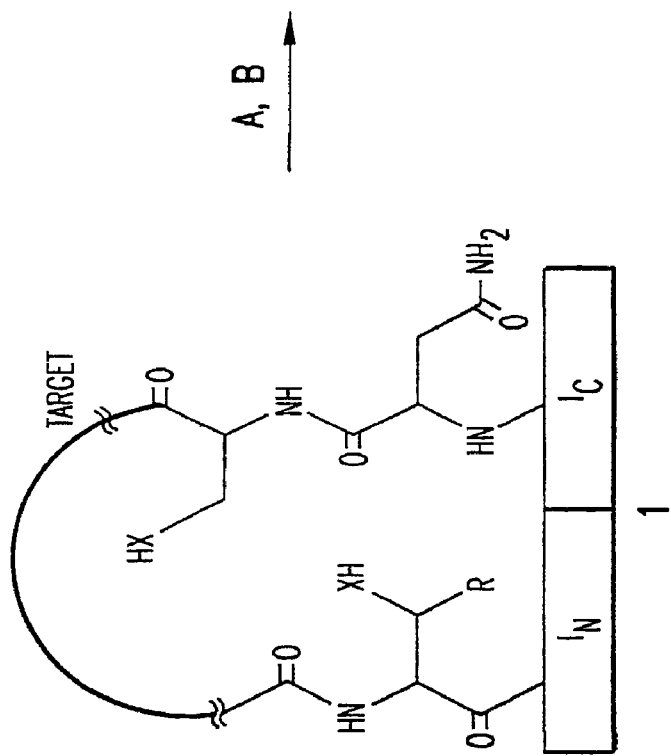
Figure 9B:
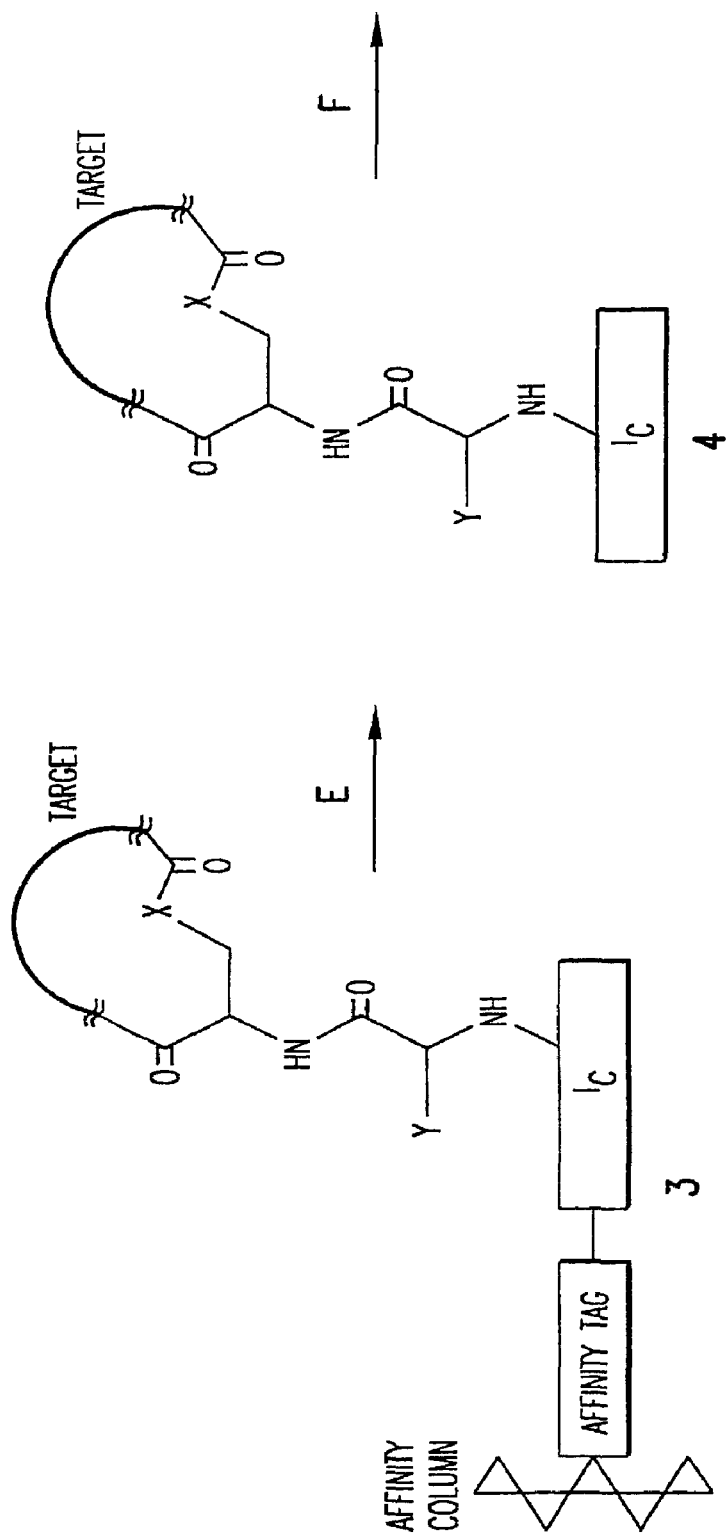
Figure 9B:
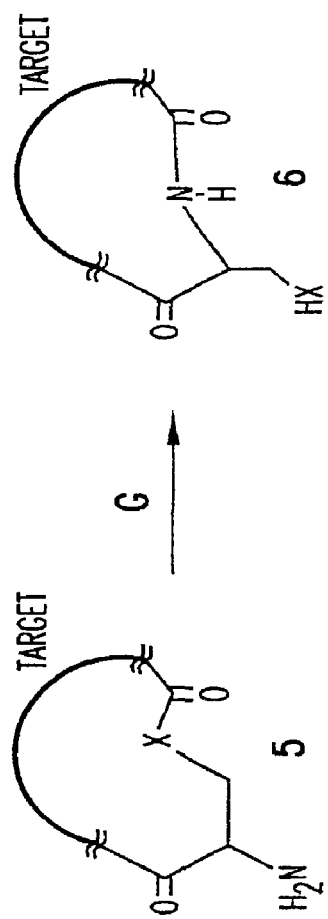

Referring now to FIG. 8, a method for purifying cyclic peptides is shown. In this method, an active intein intermediate (specie 1) is mutagenized to replace the catalytic asparagine (step A) with a non-catalytic amino acid (Y) and to introduce an affinity tag downstream of $I_N$ (step B) to yield specie 2. The intein-mediated cyclization reaction will proceed until the lariat intermediate is formed (step C). This molecule is then passed through an affinity column (step D) having a solid phase support with a ligand thereon that specifically binds the affinity tag and thus allows retention and purification of the $I_N/I_C$ non-covalent complex (specie 3). The $I_N/I_C$ reaction is then disrupted to yield a lariat intermediate (specie 4) which can be eluted from the affinity column. Proteolytic or chemical cleavage at amino acid Y (step F) liberates the lactone intermediate (specie 5). Acyl-to-N rearrangement (step G) yields the thermodynamically preferred amide cyclic product (specie 6).

Referring now to FIG. 9, a variation of the foregoing method for purifying cyclic peptides is shown. In this method, an active intein intermediate (specie 1) is mutagenized to replace the catalytic asparagine (step A) with a non-catalytic amino acid (Y) and to introduce an affinity tag upstream of $I_C$ (step B) to yield specie 2. The intein-mediated cyclization reaction will proceed until a lariat intermediate is formed (step C). This molecule is then passed though an affinity column (step D) having a solid phase support with a ligand thereon that specifically binds the affinity tag/$I_C$ intermediate (specie 3). Separation of the affinity tag (step E) from the ligand (e.g., using a molecule that competitively inhibits the tag-ligand interaction, using a high salt buffer or denaturing agent, or using a chemical reagent or protease to cleave the tag) allows recovery of the lariat intermediate (specie 4). Proteolytic or chemical cleavage at amino acid Y (step F) liberates the lactone intermediate (specie 5). Acyl-to-N rearrangement (step G) yields the thermodynamically preferred amide cyclic product (specie 6).

Method for Preparing a Library of Cyclic Peptides and Splicing Intermediates

Numerous methods of making linear peptide libraries are known in the art. Modifications of such known methods can be utilized with the methods of producing cyclic peptides and splicing intermediates taught herein to generate libraries of cyclic peptides and splicing intermediates. In general, a method of preparing a library of cyclic peptides and/or splicing intermediates includes the steps of: (a) providing a plurality of nucleic acid molecules encoding a plurality of target peptides having heterogenous amino acid sequences; (b) incorporating each of the plurality of nucleic acid molecules into an expression vector to form a plurality of expression vectors, whereby each of the plurality of nucleic acid molecules is interposed between a nucleic acid molecule encoding a first portion of a split intein and a nucleic acid molecule encoding an second portion of a split intein in each of the formed expression vectors, such that expression of the expression vectors in a host system results in the production of a plurality of splicing intermediates of cyclized forms of the target peptides or polypeptides that spontaneously splice in the host system to yield cyclized forms of the target peptides; and (c) expressing the expression vectors in the host system.

As more specific examples, the methods described in Childs et al, in *Sequence Specificity in Transcription and Translation* (Alan R. Liss, Inc., 1985) and the double strand ligation method described in Schumacher et al, Science 271: 1854, 1996 can be modified for use in the current invention. Known PCR-based methods can also be used to generate polynucleotides encoding peptides with random sequences that can be circularized or expressed as splicing intermediates in the invention. See, e.g., Caldwell and Joyce, PCR Methods Appl. 2:22, 1992; Ostermeier et al, Proc. Natl. Acad. Sci. USA 96:3562, 1999; the Nested Deletion Protocol and Reagents from Promega; and Stemmer, W. P. Nature 370:389, 1994 (DNA shuffling). The plurality of polynucleotides encoding peptides with heterogenous sequences can be incorporated as the target peptide (or the peptide to be displayed in a splicing intermediate) in the nucleic acid molecules and expression vectors of the invention as described above and then expressed in a host system to make a library of cyclic peptides or splicing intermediates.

Method for Screening a Cyclic Peptide for a Predetermined Characteristic

Myriad techniques exist for screening small molecules for particular characteristics. See, e.g., Fernades, P., Current Opin. Chem. Biol. 2:597, 1998; Science 286:1759, 1999; U.S. Pat. Nos. 5,585,277 and 5,989,814. More specifically, methods for determining which peptide in a combinatorial peptide library binds specifically to a target protein are also known. E.g., U.S. Pat. No. 5,834,318. Many of these methods can be adapted to screen cyclic peptides and/or splicing intermediates made with the methods of the invention for particular characteristics.

A general method of screening a peptide molecule for a predetermined characteristic includes the steps of: (a) providing a nucleic acid molecule that encodes a polypeptide having a target peptide interposed between a first portion of a split intein and a second portion of a split intein such that expression of the nucleic acid molecule in a host system produces the peptide molecule either as a cyclized form of the target peptide (as a result of spontaneously splicing of the polypeptide in the host system) or a splicing intermediate of a cyclized form of the target peptide; (b) providing the host system; (c) introducing the isolated nucleic acid molecule in the host system; (d) placing the host system under conditions that cause the peptide molecule to be produced; and (e) testing the peptide molecule for the predetermined characteristic.

Step (a) can be performed as described elsewhere herein by, for example, using molecular biology techniques (see, Ausubel et al and Sambrook et al, supra) to produce polynucleotides encoding the target peptide, the first portion of an intein, and the second portion of an intein. The resulting three polynucleotides can then be fused (e.g., ligated) together to form the nucleic acid molecule. The host system provided can be any of those described herein in which the nucleic acid molecule can be expressed (e.g., a bacterium, a yeast, a mammalian cell, etc.). The nucleic acid can be introduced into the host system by known methods depending on the form of the nucleic acid molecule and the host system used. For example, the nucleic acid molecules can be introduced into a cell by electroporation, lipofection, using calcium chloride-mediated transformation, using a gene "gun," using a bacteriophage vector (when host system is a bacterium), using a plasmid construct, using a viral vector, etc.

The host system can be placed under conditions that cause the peptide molecule to be produced by adjusting the conditions according to the particular form of the nucleic acid molecule and the host system used. For a human cell host system, this can mean placing the cell in an appropriate nutrient rich medium and culturing the cell in a 37° C., humidified, 5-10% $CO_2$ incubator. For inducible expression vectors, this can mean adding the substance to the host system that induces expression of the nucleic acid molecule in the vector. For example, when using an arabinose-inducible expression vector, this step can include adding arabinose to the host system.

Testing of the peptide molecule for the predetermined characteristic can be performed by a large number of different methods, e.g., measuring binding of the peptide molecule to a known ligand and analyzing the ability of the peptide molecule to modulate (i.e., increase or decrease the rate of) a biochemical reaction. For a description of various methods that may be used for testing peptides for predetermined characteristics see, Fernades, P., supra.

More specific exemplary methods that may be used to screen cyclic peptides or splicing intermediates for a particular characteristic include using a solid phase support and affinity chromatography to identify molecules which specifically bind cyclic peptides or splicing intermediates; using phage display technology; and using aptamer peptide fusion constructs and/or hybrid systems to identify cyclic peptides or splicing intermediates that can modulate a specific biochemical reaction or intracellular event.

Solid Phase Supports/Affinity Chromatography For Identifying Molecules That Interact with Cyclic Peptides and/or Splicing Intermediates Cyclic peptides or splicing intermediates can be immobilized on a solid phase support to facilitate identification and/or purification of molecules that specifically bind a given cyclic peptide or splicing intermediate. For a general overview of peptide affinity columns for purification see Bumbach, G. A. and D. J. Hammond, Biopharm., 5:24, 1992. Below are examples of how this can be performed in the invention.

Figure 10A:
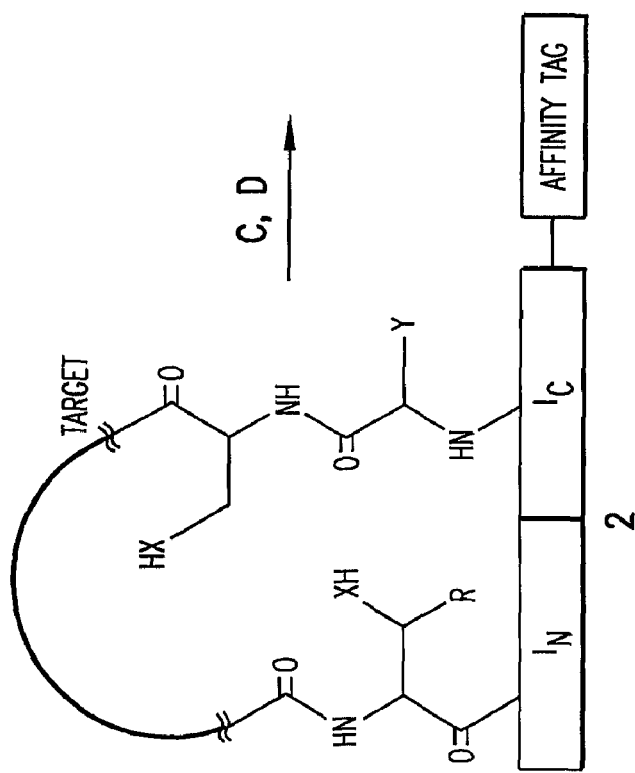
FIG. 10 is a schematic illustration of a solid phase support/affinity chromatography-based method for identifying/purifying molecules which specifically bind a splicing intermediate.
Figure 10A:
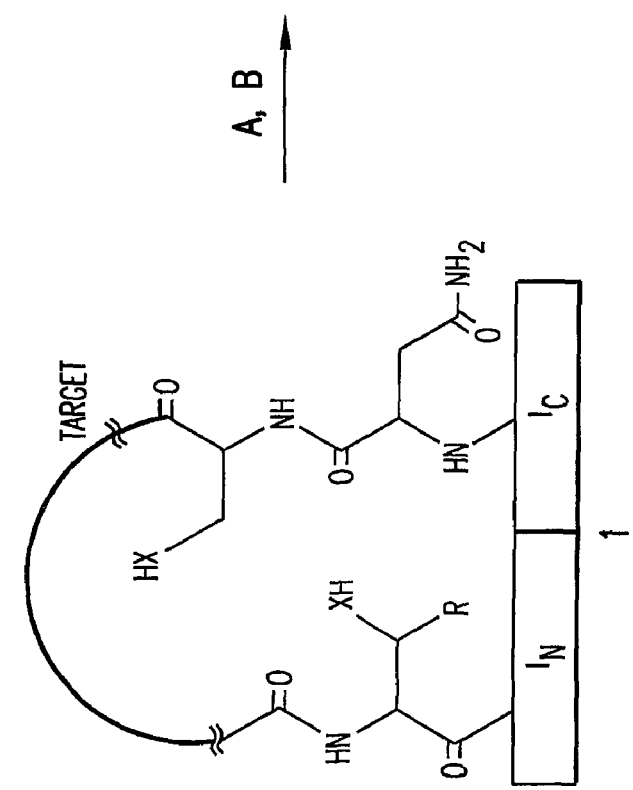
Figure 10B:
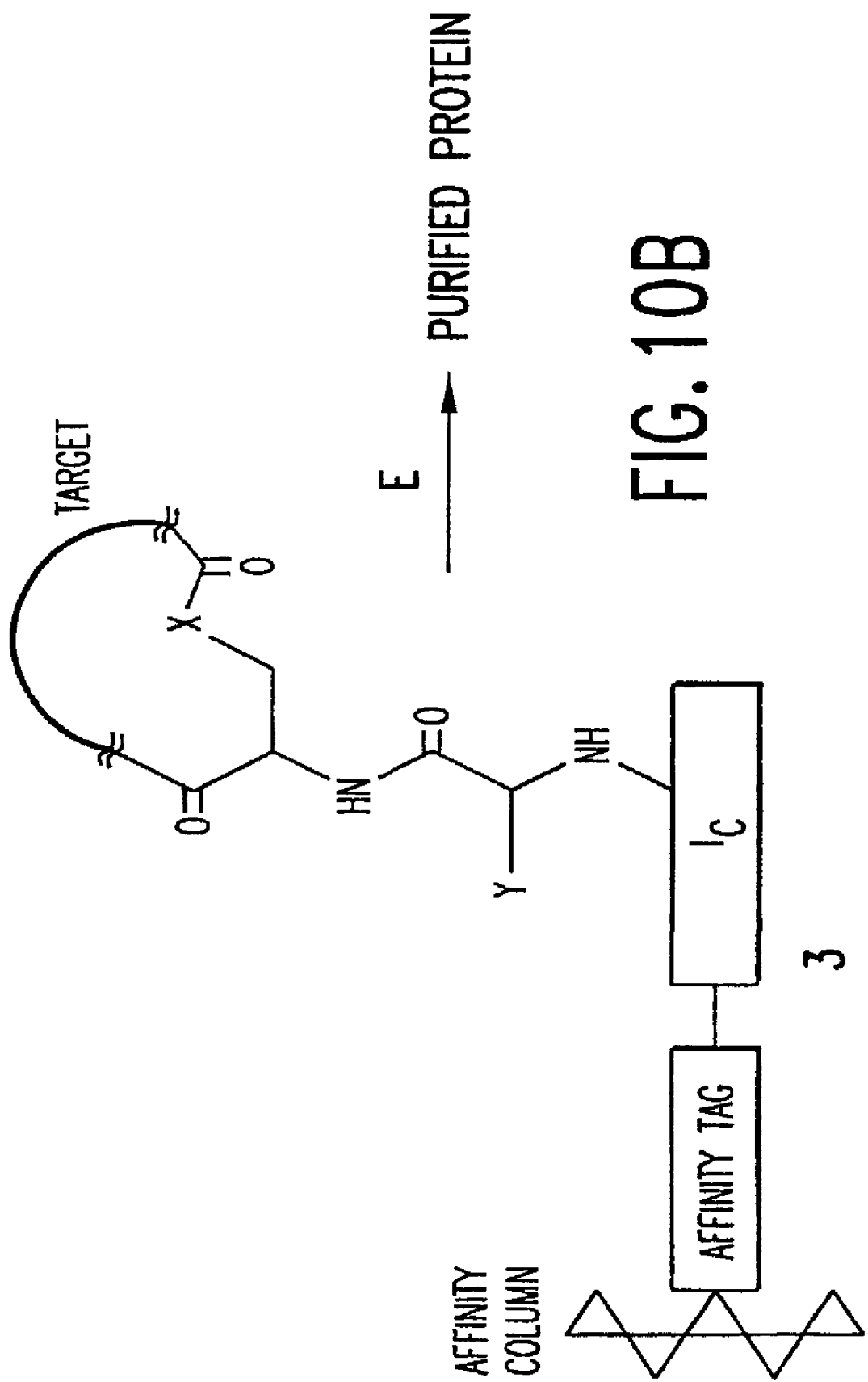

Referring now to FIG. 10, a method for identifying/purifying molecules that specifically bind a given splicing intermediate is shown. In this method, an active intein intermediate (specie 1) is mutagenized to replace the catalytic asparagine (step A) with a non-catalytic amino acid (Y) and to introduce an affinity tag upstream of $I_C$ (step B) to yield specie 2. The intein-mediated cyclization reaction will proceed until a lariat intermediate is formed (step C). This molecule is then passed though an affinity column (step D) having a solid phase support with a ligand thereon that specifically binds the affinity tag/$I_C$ intermediate (specie 3). A solution containing target molecules (i.e., candidates for binding the splicing intermediates) is then passed through the column (step E). Target molecules that specifically bind the splicing intermediate are selectively retained within the column. These target molecules can be removed from the column and biochemically analyzed (e.g., sequenced).

Figure 11A:
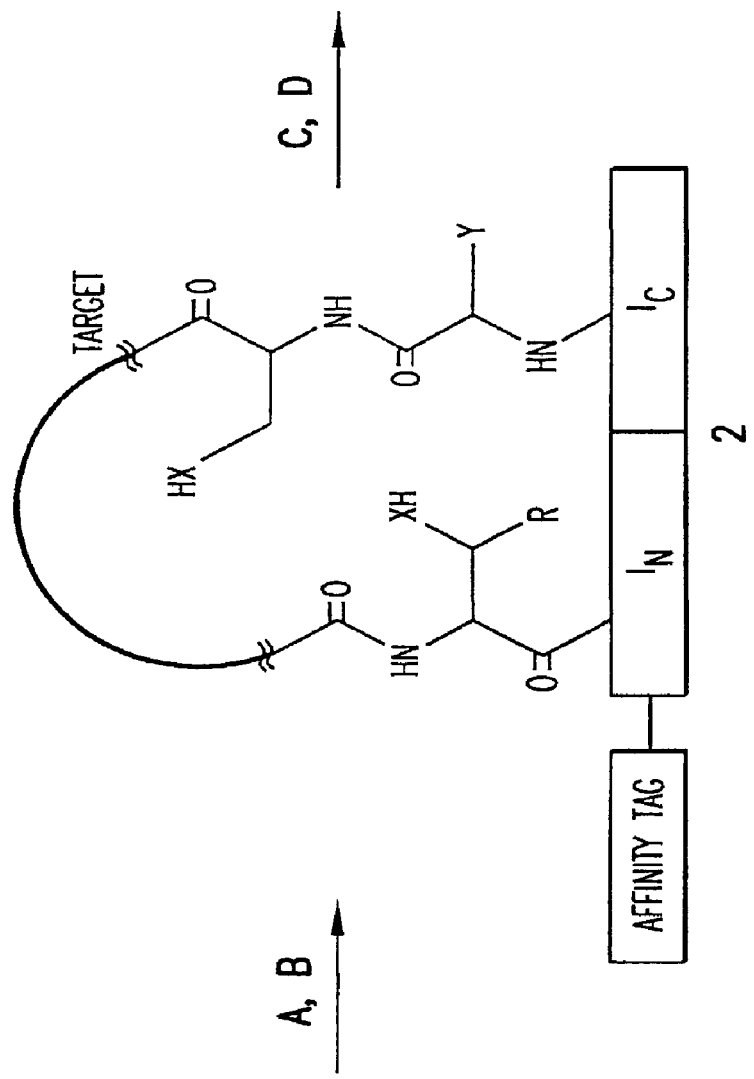
FIG. 11 is a schematic illustration of another solid phase support/affinity chromatography-based method for identifying/purifying molecules which specifically bind a splicing intermediate.
Figure 11A:
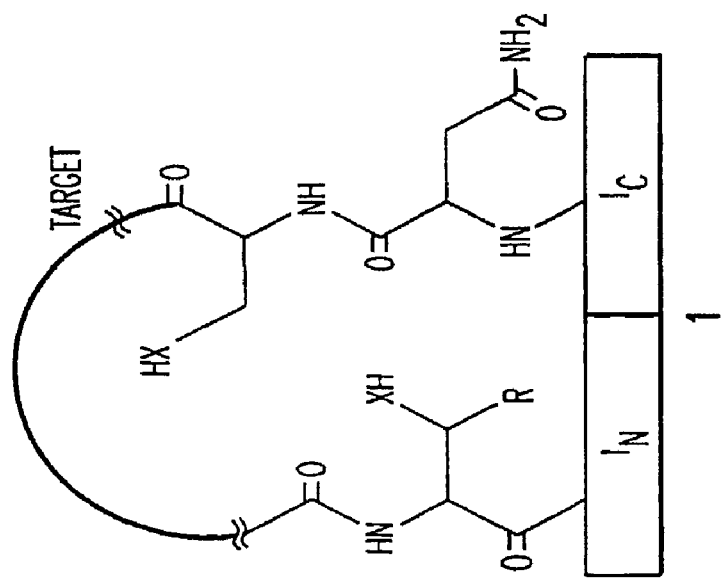
Figure 11B:
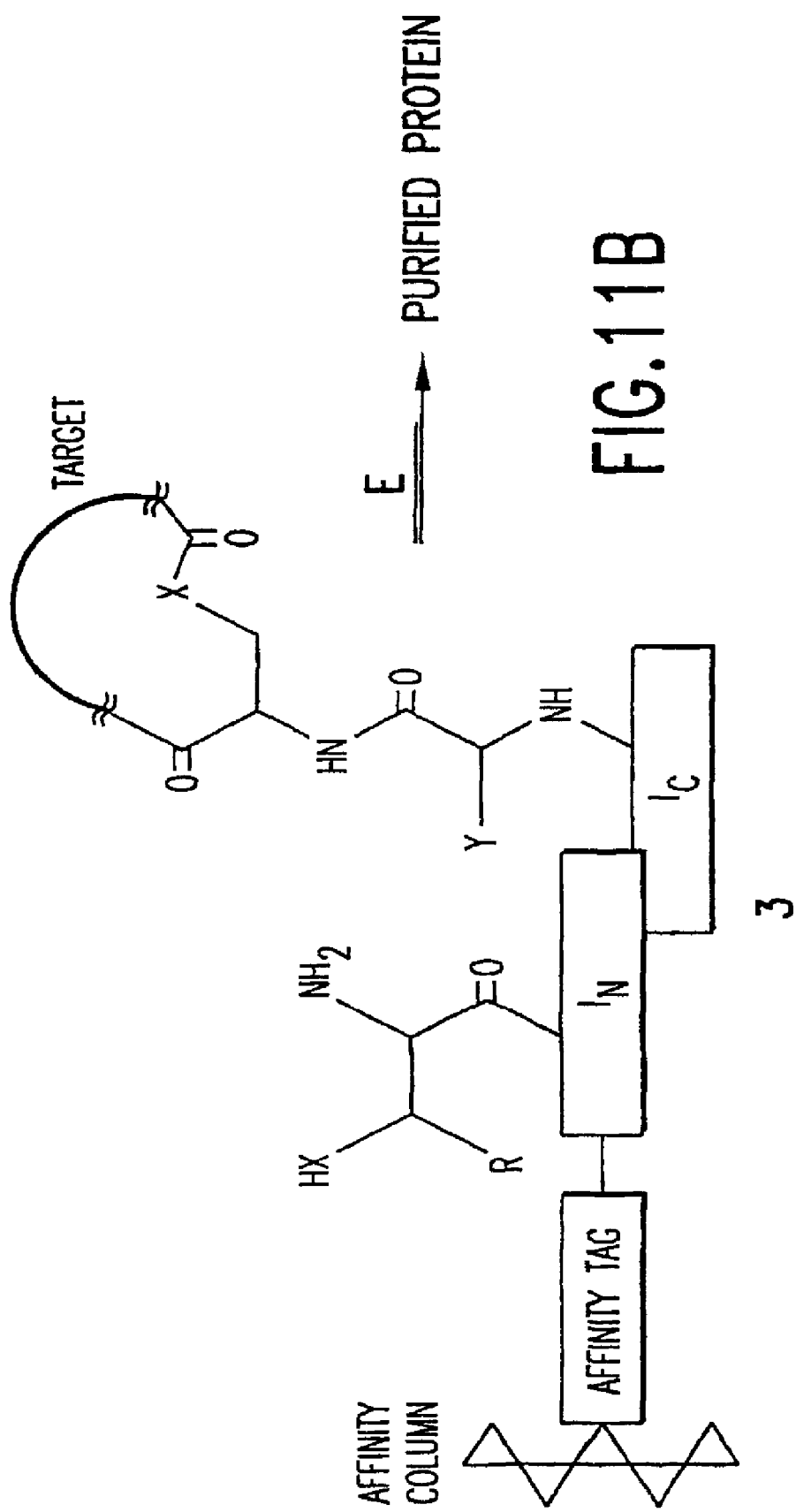

Referring now to FIG. 11, another method for identifying/purifying molecules which specifically bind a given splicing intermediate is shown. In this method, an active intein intermediate (specie 1) is mutagenized to replace the catalytic asparagine (step A) with a non-catalytic amino acid (Y) and to introduce an affinity tag downstream of $I_N$ (step B) to yield specie 2. The intein-mediated cyclization reaction will proceed until a lariat intermediate is formed (step C). This molecule is then passed though an affinity column (step D) having a solid phase support with a ligand thereon that specifically binds the affinity tag to allow the retention and purification of the $I_N$/$I_C$ non-covalent complex (specie 3). Cleavage of the affinity tag (step E) allows recovery of the lariat intermediate (specie 4). A solution containing target molecules (i.e., candidates for binding the splicing intermediates) is then passed through the column (step E). Target molecules that specifically bind the splicing intermediate are selectively retained within the column.

Figure 12A:
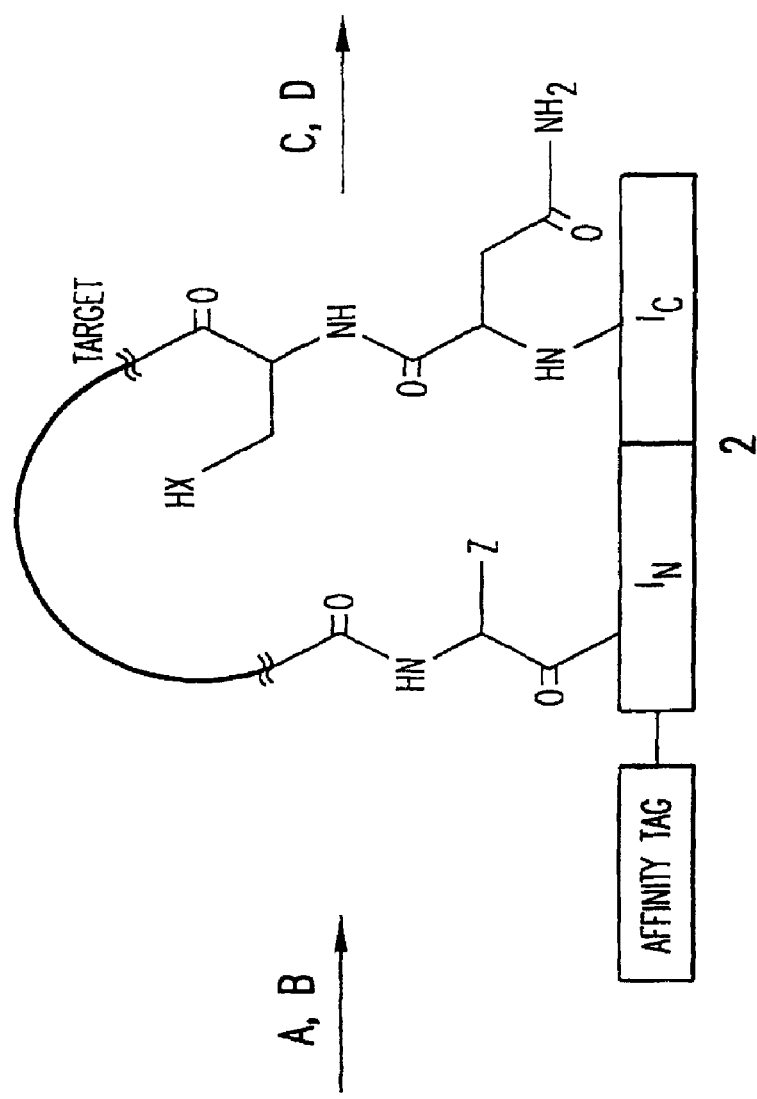
FIG. 12 is a schematic illustration of another solid phase support/affinity chromatography-based method for identifying/purifying molecules which specifically bind a splicing intermediate.
Figure 12A:
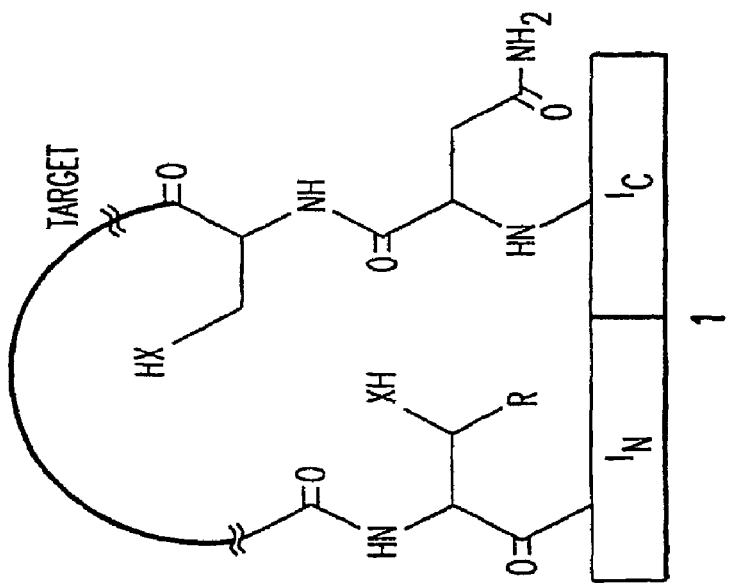
Figure 12B:
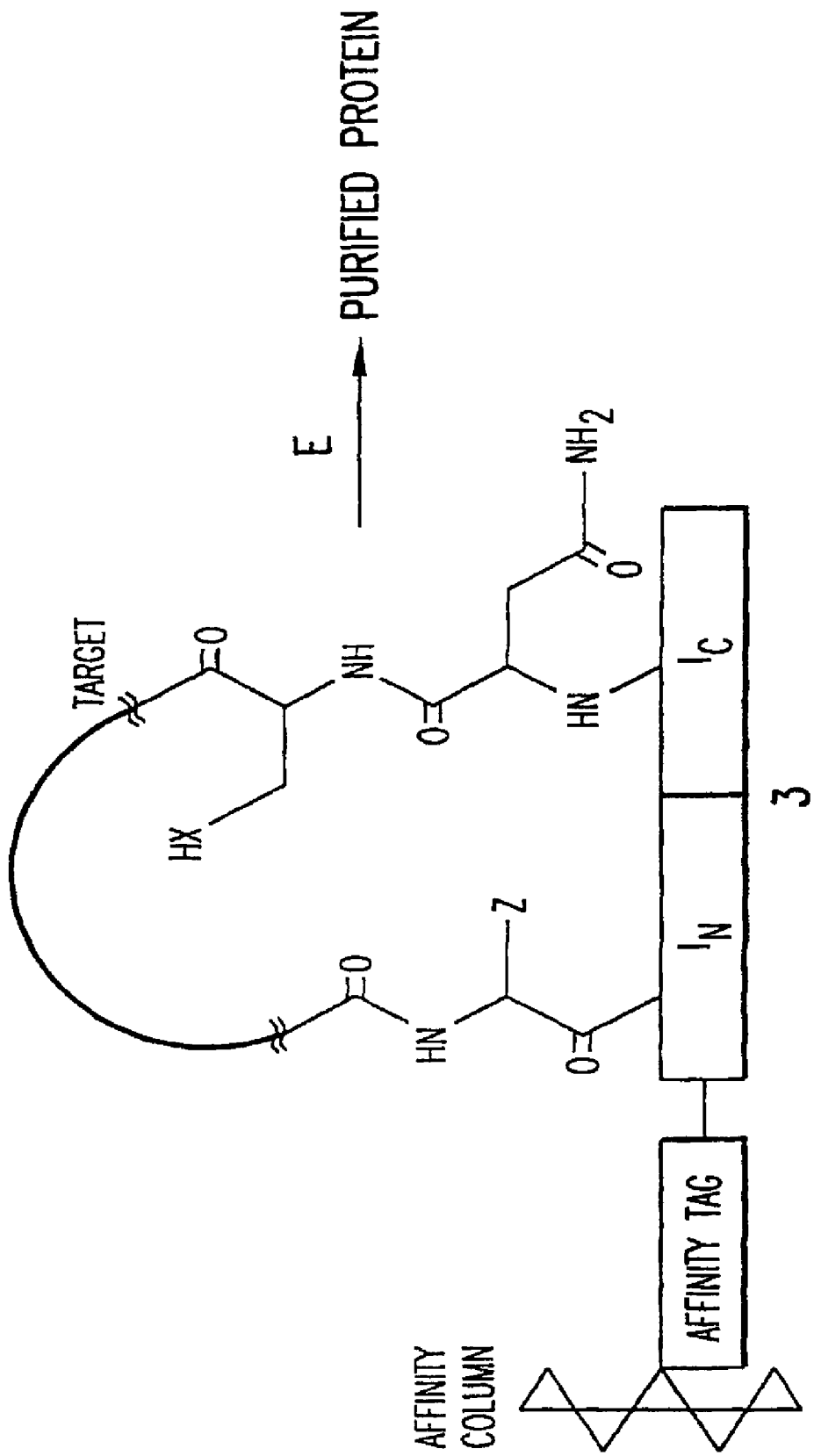

Referring now to FIG. 12, another method for identifying/purifying molecules that specifically bind a given splicing intermediate is shown. In this method, an active intein intermediate (specie 1) is mutagenized to replace the $I_N$ nucleophile (step A) with a non-catalytic amino acid (Z) and to introduce an affinity tag downstream of $I_N$ (step B) to yield an $I_C$-peptide-$I_N$-tag fusion protein (specie 2). The intein-mediated cyclization reaction will produce the fusion protein (step C). This protein is then passed though an affinity column (step D) having a solid phase support with a ligand thereon that specifically binds the affinity tag to allow the retention and purification of the protein complex (specie 3). A solution containing target molecules (i.e., candidates for binding the splicing intermediates) is then passed through the column (step E). Target molecules that specifically bind the splicing intermediate are selectively retained within the column.

Figure 13A:
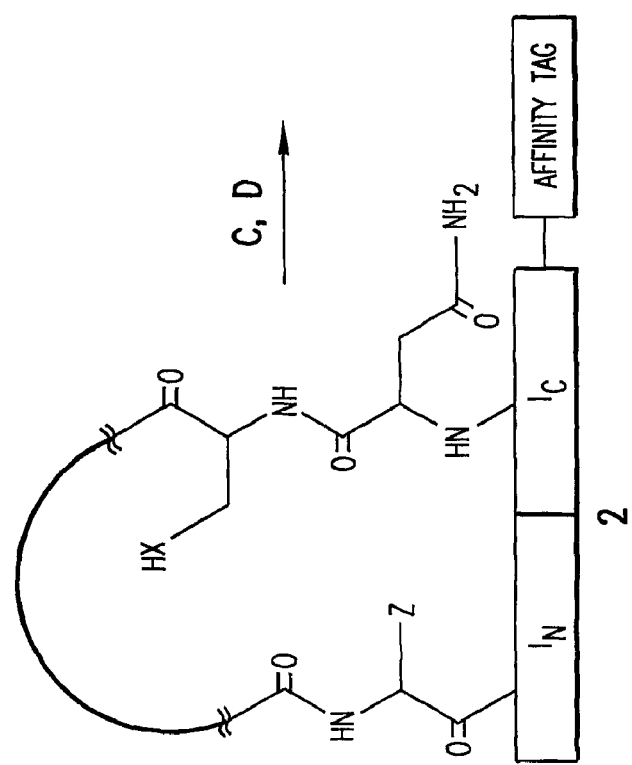
FIG. 13 is a schematic illustration of another solid phase support/affinity chromatography-based method for identifying/purifying molecules which specifically bind a splicing intermediate.
Figure 13A:
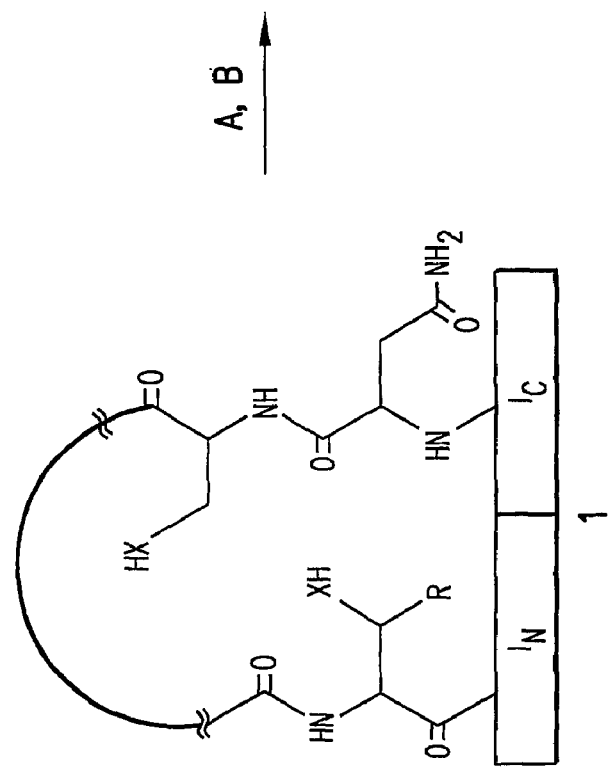
Figure 13B:
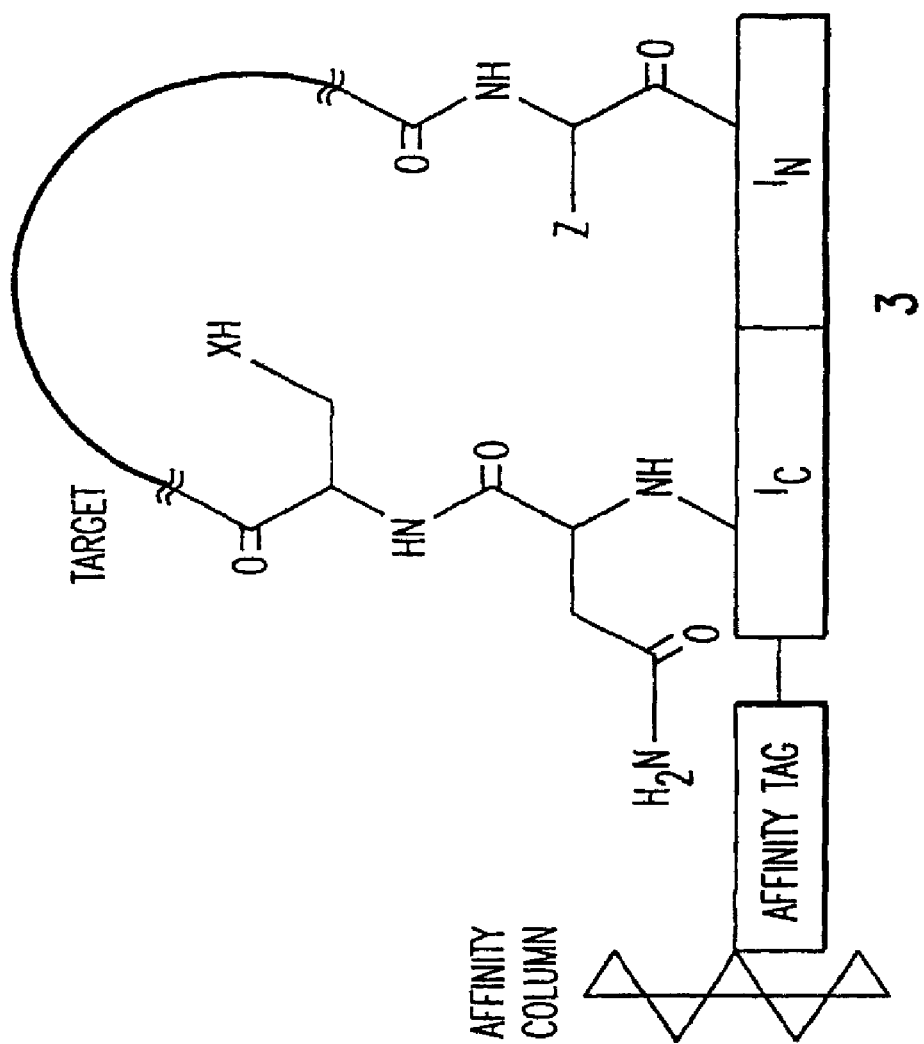

Referring now to FIG. 13, yet another method for identifying/purifying molecules which specifically bind a given splicing intermediate is shown. In this method, an active intein intermediate (specie 1) is mutagenized to replace the $I_N$ nucleophile (step A) with a non-catalytic amino acid (Z) and to introduce an affinity tag upstream of $I_C$ (step B) to yield an tag-$I_C$-peptide-$I_N$ fusion protein (specie 2). The intein-mediated cyclization reaction will produce the fusion protein (step C). This protein is then passed though an affinity column (step D) having a solid phase support with a ligand thereon that specifically binds the affinity tag to allow the retention and purification of the protein complex (specie 3). A solution containing target molecules (i.e., candidates for binding the splicing intermediates) is then passed through the column (step E). Target molecules that specifically bind the splicing intermediate are selectively retained within the column.

Phage Display

Methods of screening molecules using phage display are also within the invention. Conventional methods using phage display can be modified by using the phage to display the cyclic peptides and/or splicing intermediates of the invention. For example, if Z in FIG. 1 is a phage coat protein and XH=H in FIG. 2, the splicing reaction will not progress beyond the first ester intermediate, thus resulting in the target peptide being displayed as a loop. In this manner, libraries comprising phage particles displaying loop target peptides can be prepared and used to pan for molecules that bind the displayed loop. For instance, a target molecule can immobilized on a solid phase support. Phage libraries displaying different looped peptides can then be mixed with the support. Those phage displaying looped peptides that bind the target molecule would be selectively retained on the support. After elution from the support (e.g., by cleavage of the ester linkage of the phage-displayed loop peptides with high concentrations of a potent nucleophile), the amino acid sequences of the looped peptides can be determined by standard molecular biology methods.

Aptamers

Peptides aptamers are polypeptides that contain a conformationally constrained target peptide region of variable sequence displayed from a scaffold. Since cyclic peptides or splicing intermediates can function as aptamers, known methods of analyzing aptamers can be modified to assist in identifying particular characteristics of the cyclic peptides or splicing intermediates. See, e.g., Geyer et al, Proc. Natl. Acad. Sci. USA 96:8567, 1999; Caponigro et al, Proc. Natl. Acad. Sci. USA 95:7508, 1998; Mikhail et al, Proc. Natl. Acad. Sci. USA 95:14266, 1998; Norman et al, Science 285: 591, 1999.

Figure 14:
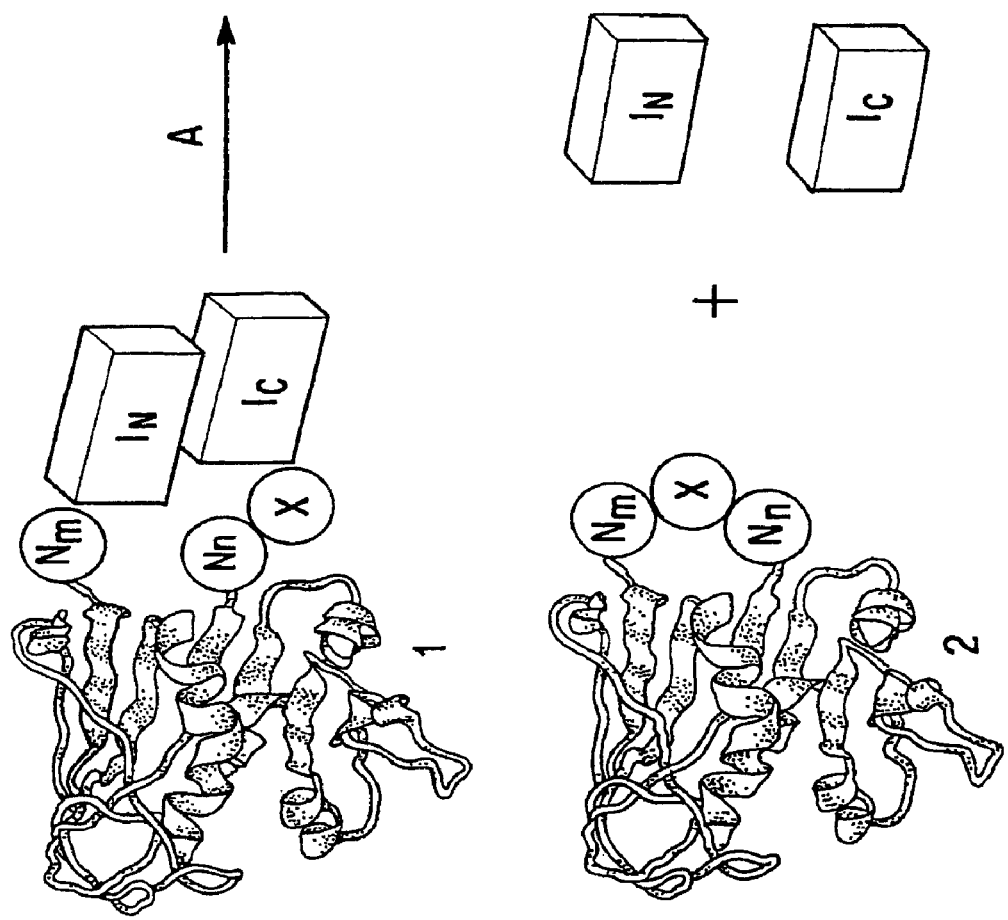
FIG. 14 is a schematic illustration of the use of aptamer scaffolds in the invention.
Figure 15A:
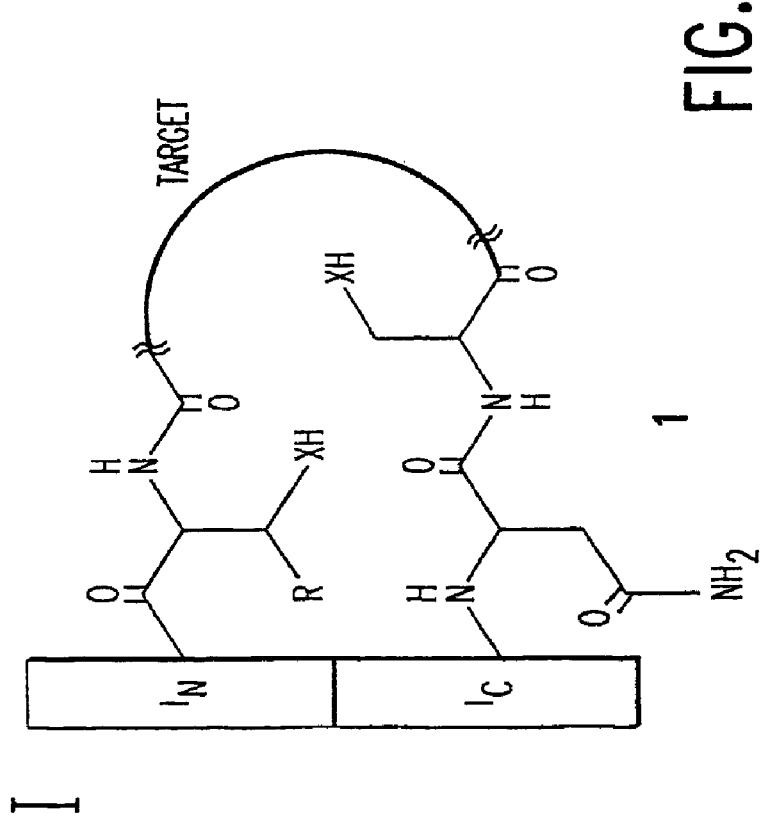
FIG. 15 is a schematic illustration of two reactions for preparing aptamers within the invention.
Figure 15A:
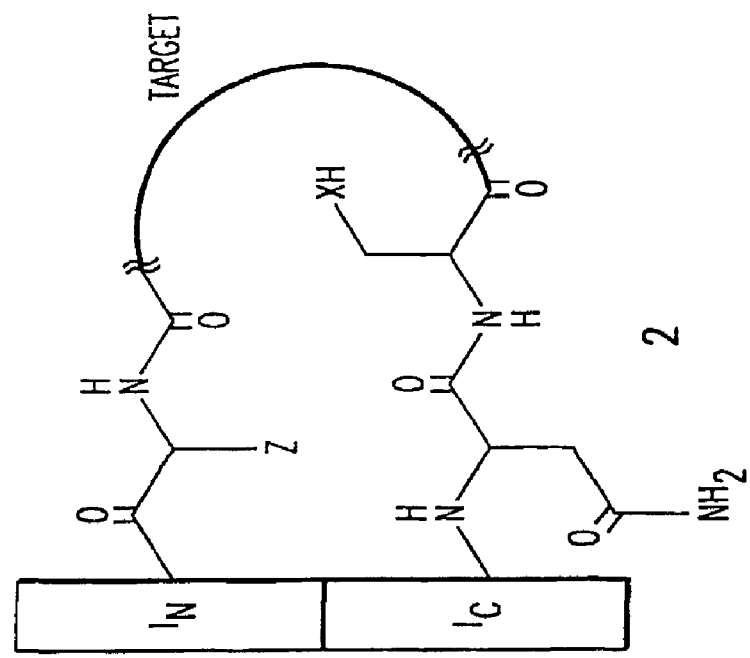
Figure 15B:
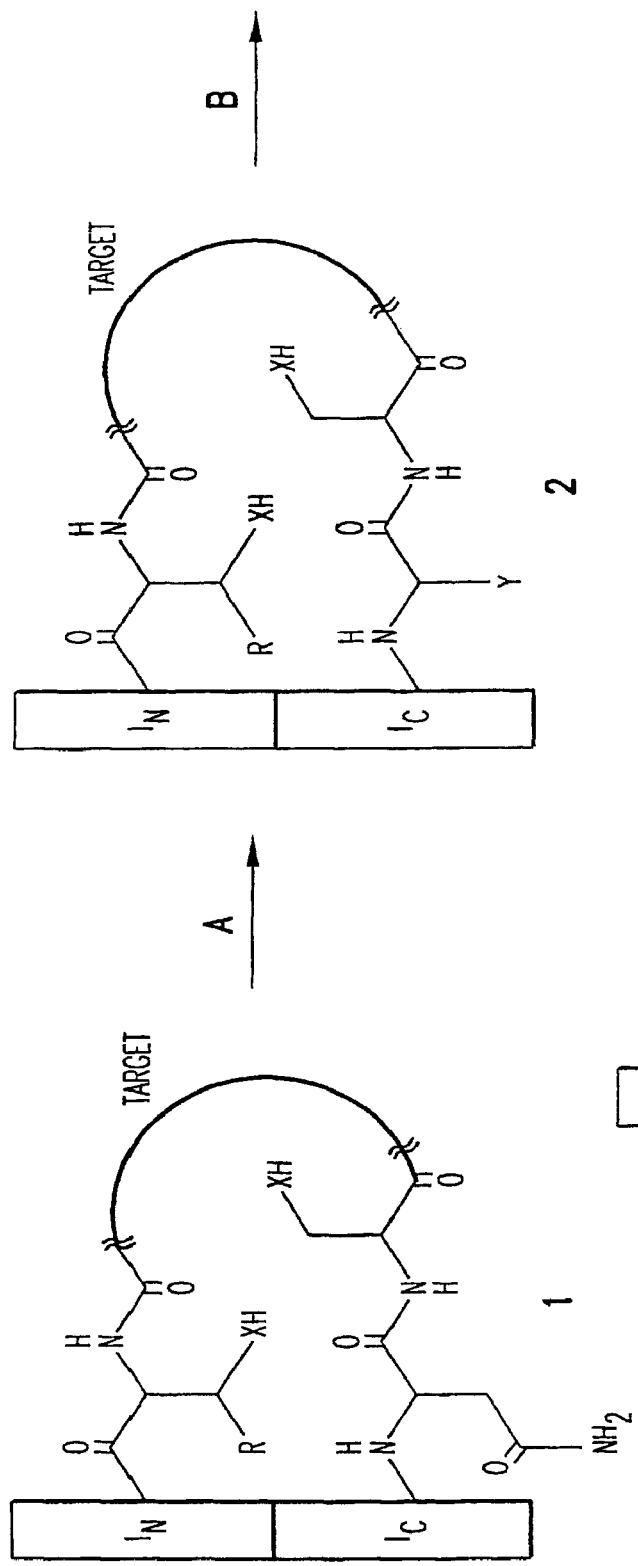
Figure 15B:
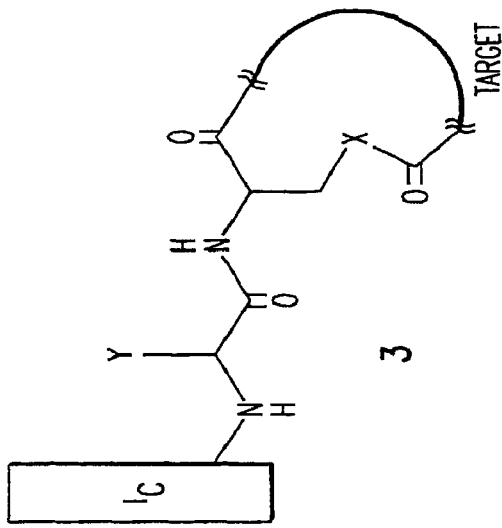

For example, referring to FIG. 14, cyclic proteins can be used as aptamer scaffolds in a technique that allows members of a peptide library to be displayed as a constrained loop between the N-terminus and C-terminus of the cyclic protein scaffold. As shown in FIG. 14, an aptamer library can be expressed as an $I_C$-scaffold-$I_N$ fusion protein (specie 1). Procession of the intein-mediated cyclization reaction in vivo (step A) yields an $I_N$, an $I_C$, and a cyclic scaffold protein (specie 2). The aptamer library is displayed in the linker region between the N-terminus and C-terminus. In FIG. 14, N represents any amino acid and the subscripts n and m are any integral number equal or greater than 0, and X represents serine, threonine, or cysteine.

Other examples of using aptamers are also within the invention. Referring to FIG. 15, two such methods are described. In reaction I, an active intein intermediate is mutagenized to replace the nucleophilic amino acid from $I_N$ (step A) with a non-catalytic amino acid (Z). These processes inactivate the splicing reaction to yield specie 2. Because of the strong interaction between $I_C$ and $I_N$, this technique allows the members of a peptide library to be displayed as a constrained loop in the linker region between the two intein portions (Target). In reaction II, an active intein intermediate is mutagenized to replace the catalytic asparagine (step A) with a non-catalytic amino acid (Y) to yield specie 2. Progression of the intein-mediated cyclization reaction proceeds in vivo (step B) and arrests at the lariat intermediate stage (specie 3), allowing members of a peptide library to be displayed as a constrained lactone.

Hybrid Systems

The yeast two-hybrid system is a well-studied method for analyzing in vivo protein-protein interactions. Fields, S. and O. Song, Nature (London) 340:245, 1989. It and variations thereof such as one-hybrid systems, three-hybrid systems, reverse two-hybrid system, split-hybrid system, alternative n-hybrid systems, small molecule-based hybrid systems can be used to analyze the characteristics of cyclic peptides and/or splicing intermediates by adapting known methods. See, e.g., Drees, B. L., Current Opin. Chem. Biol., 3:64, 1999; Vidal, M., and P. Legrain, Nucleic Acids Research, 27:919, 1999; Current Protocols in Molecular Biology, eds., Ausubel, F. M., et al, Wiley, New York, 1996; Huang, J. and S. L. Schreiber, Proc. Natl. Acad. Sci. (USA) 94:13396, 1997; Yang, M., et al, Nucleic Acids Res. 23:1152, 1995; Colas, P., et al, Nature (London), 380:548, 1996; Xu, C. W., et al, Proc. Natl. Acad. Sci. (USA) 94:12473, 1997.

Figure 16A:
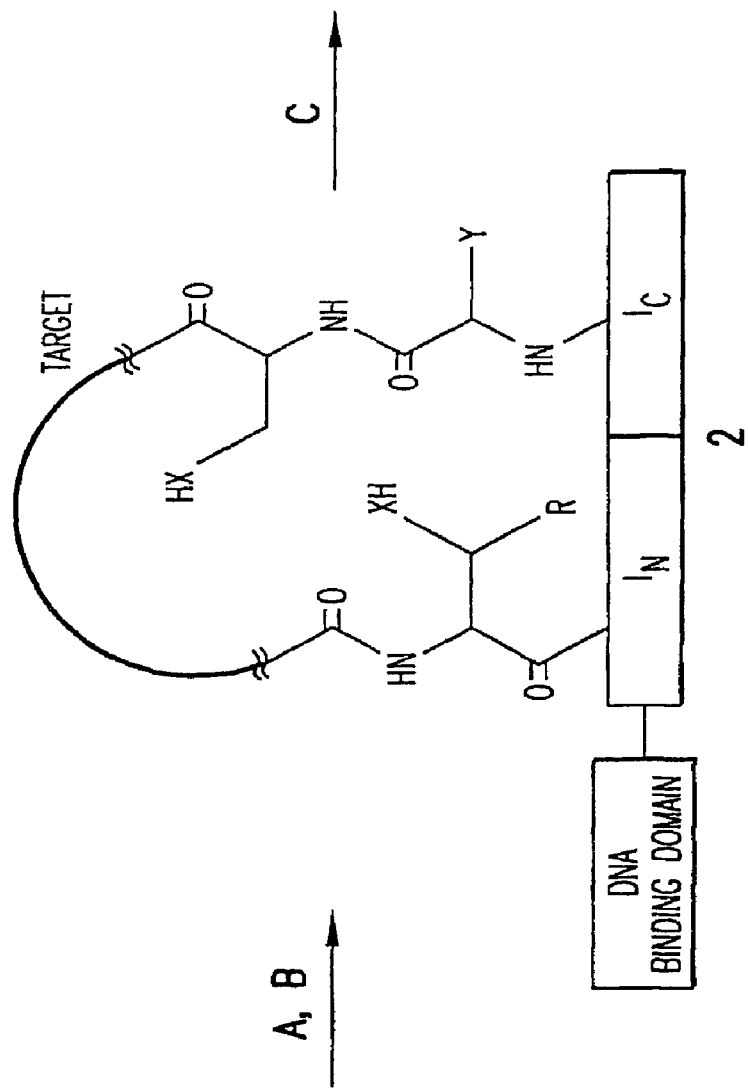
FIG. 16 is a schematic illustration of a method for screening within the invention.
Figure 16A:
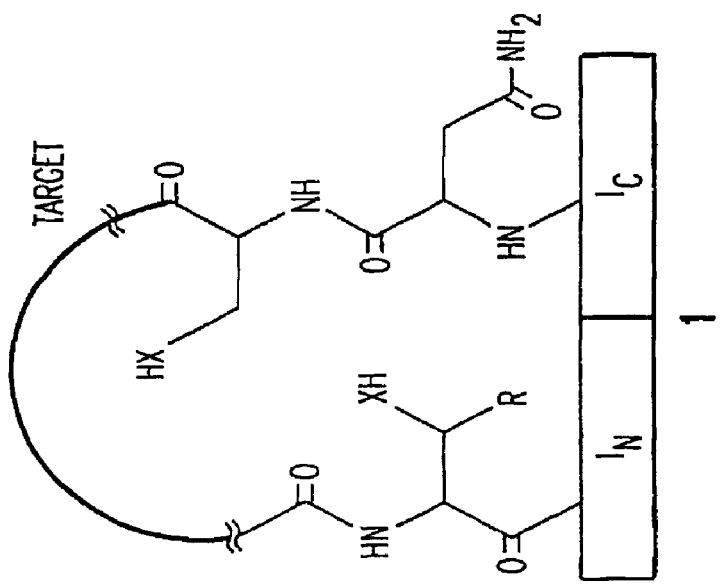
Figure 16B:
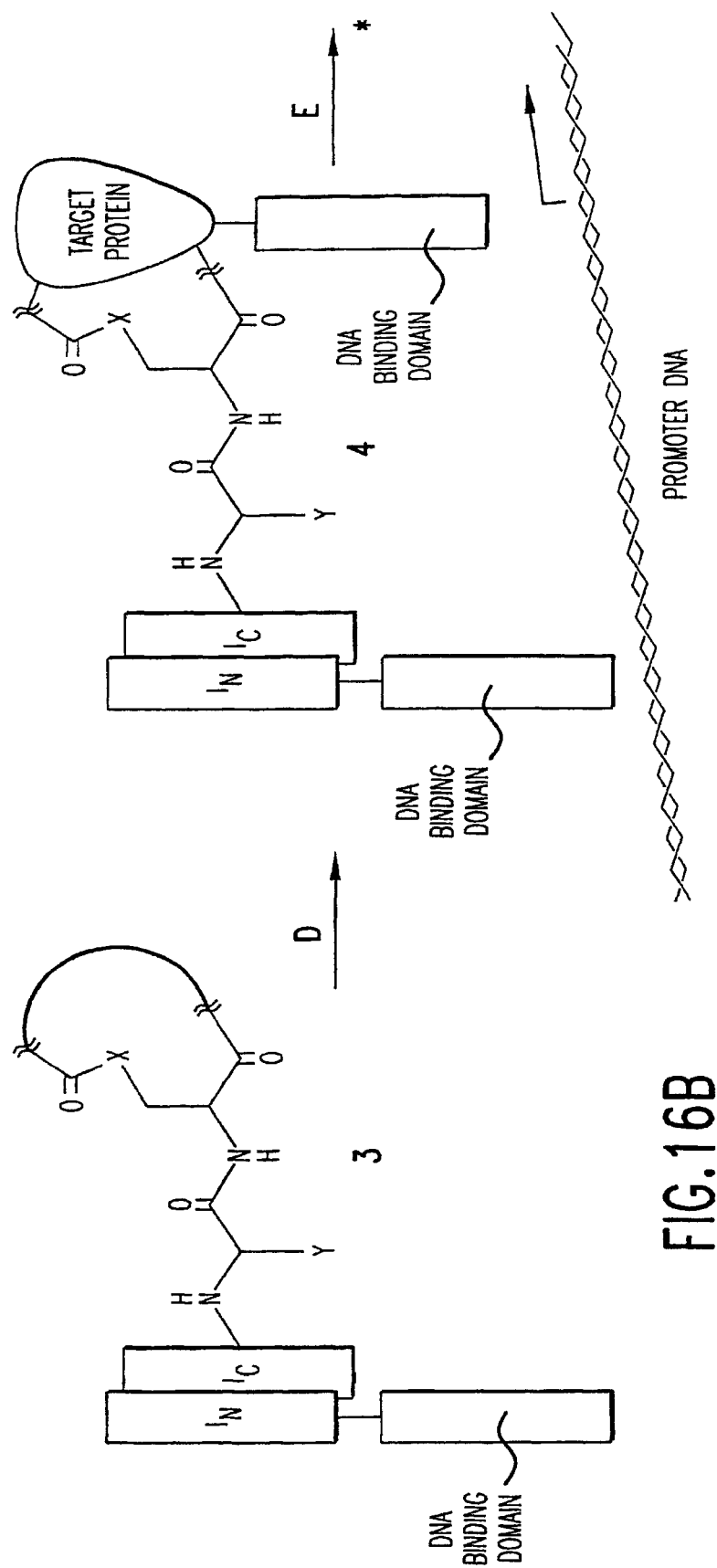

For example, referring to FIG. 16, a method of identifying a target protein that interacts with a splicing intermediate is within the invention. In this method, an active intein intermediate (specie 1) is mutagenized to replace the catalytic asparagine (step A) with a non-catalytic amino acid (Y) and to introduce a DNA-binding domain downstream of $I_N$ (step B) to yield specie 2. The intein-mediated cyclization reaction will proceed until the lariat intermediate (specie 3) is formed (step C). $I_N$ and $I_C$ form a strong non-covalent complex. The resulting lariat intermediate is then co-expressed with a target protein attached to a DNA-binding domain (step D). Interaction of the lariat intermediate with the target protein (specie 4) causes activation of a promoter region (step E) leading to expression of the reporter gene (*). This method allows identification of target molecules able to bind the lariat intermediate. This method can be modified such that a known molecule (in place of an unknown target protein) is attached to a DNA-binding domain, so that lariat intermediates displaying a looped peptide that binds the known molecule can be identified.

Figure 17A:
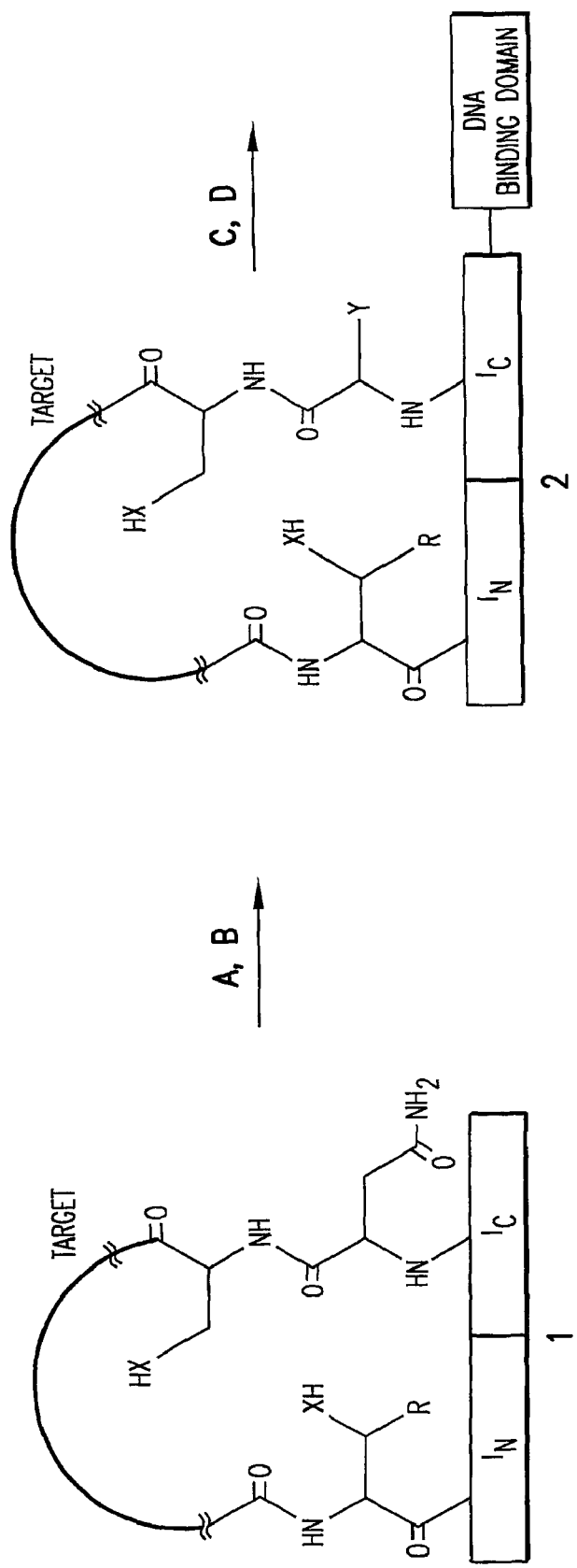
FIG. 17 is a schematic illustration of another method for screening within the invention
Figure 17B:
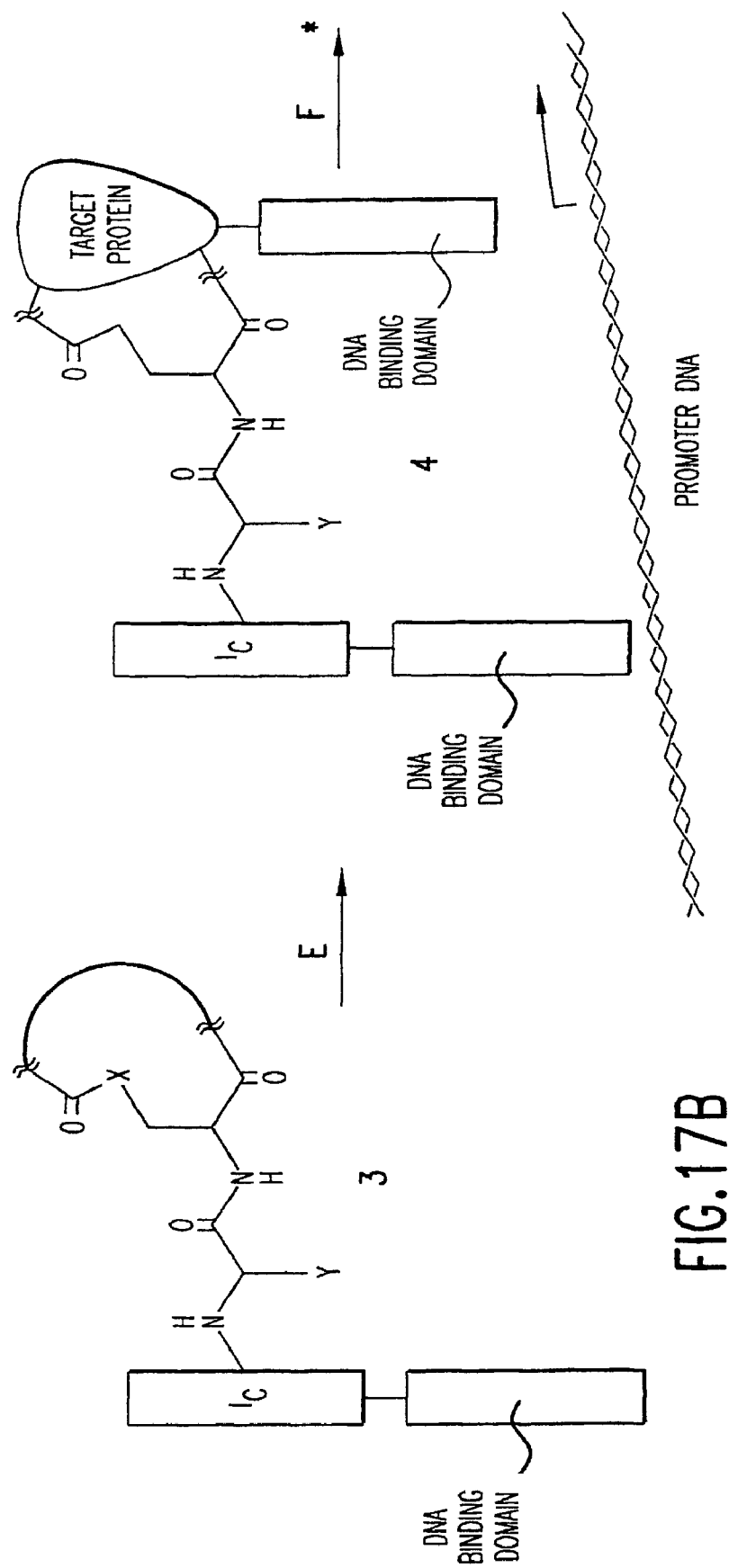

Referring to FIG. 17, another method for identifying a target protein that interacts with a splicing intermediate is described. In this method, an active intein intermediate (specie 1) is mutagenized to replace the catalytic asparagine (step A) with a non-catalytic amino acid (Y) and to introduce a DNA-binding domain upstream of $I_C$ (step B) to yield specie 2. The intein-mediated cyclization reaction will proceed until the lariat intermediate (specie 3) is formed (step C). This molecule is then co-expressed with a target protein attached to a DNA-binding domain (step D). Interaction of the lariat intermediate with the target protein (specie 4) causes activation of a promoter region (step E) leading to expression of the reporter gene (*). This method allows identification of target molecules able to bind the lariat intermediate. This method can be modified such that a known molecule (in place of an unknown target protein) is attached to a DNA-binding domain, so that lariat intermediates displaying a looped peptide that binds the known molecule can be identified.

Figure 18A:
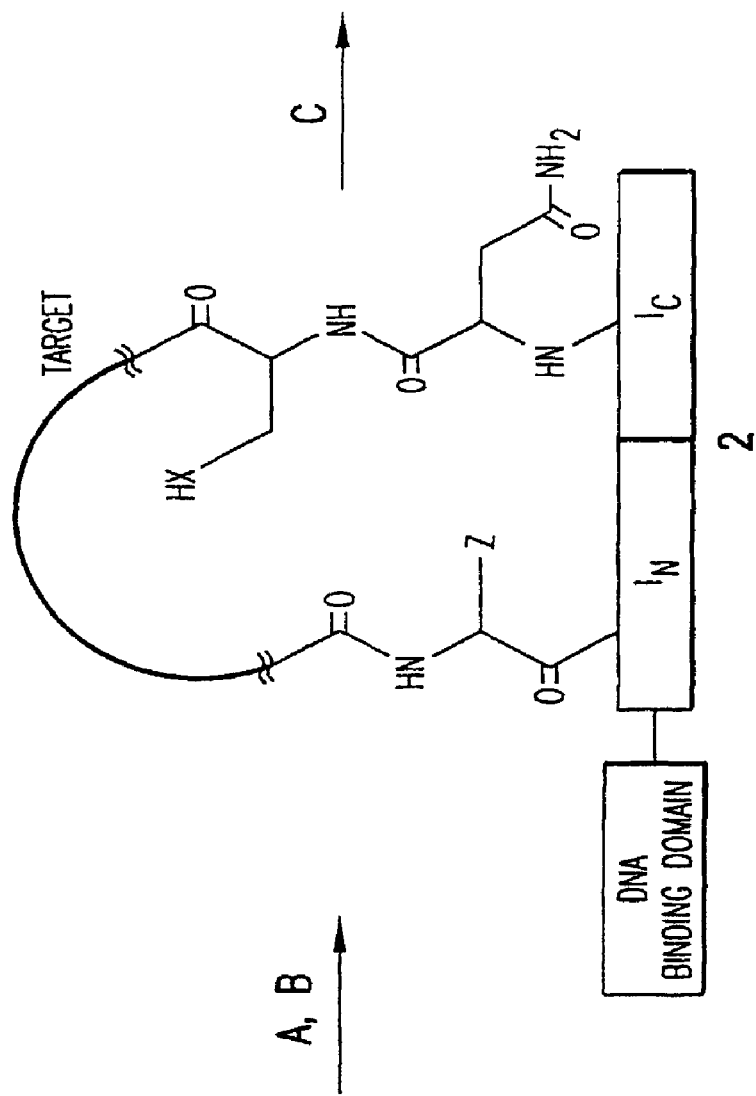
FIG. 18 is a schematic illustration of another method for screening within the invention.
Figure 18A:
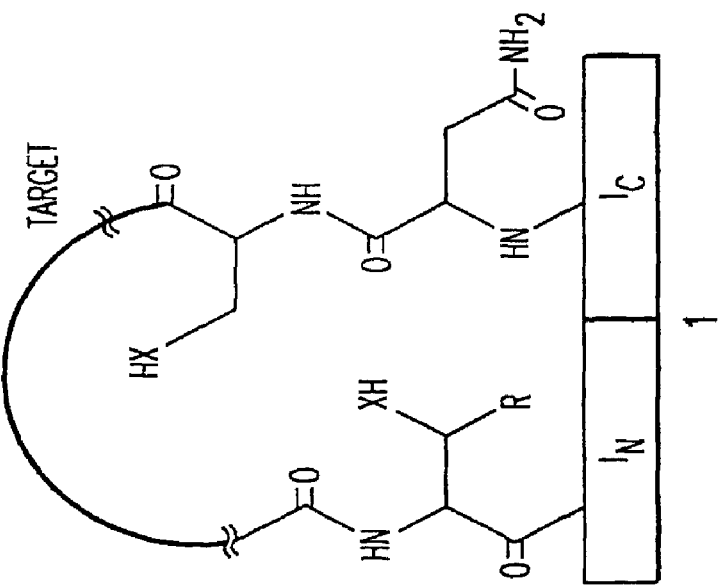
Figure 18B:
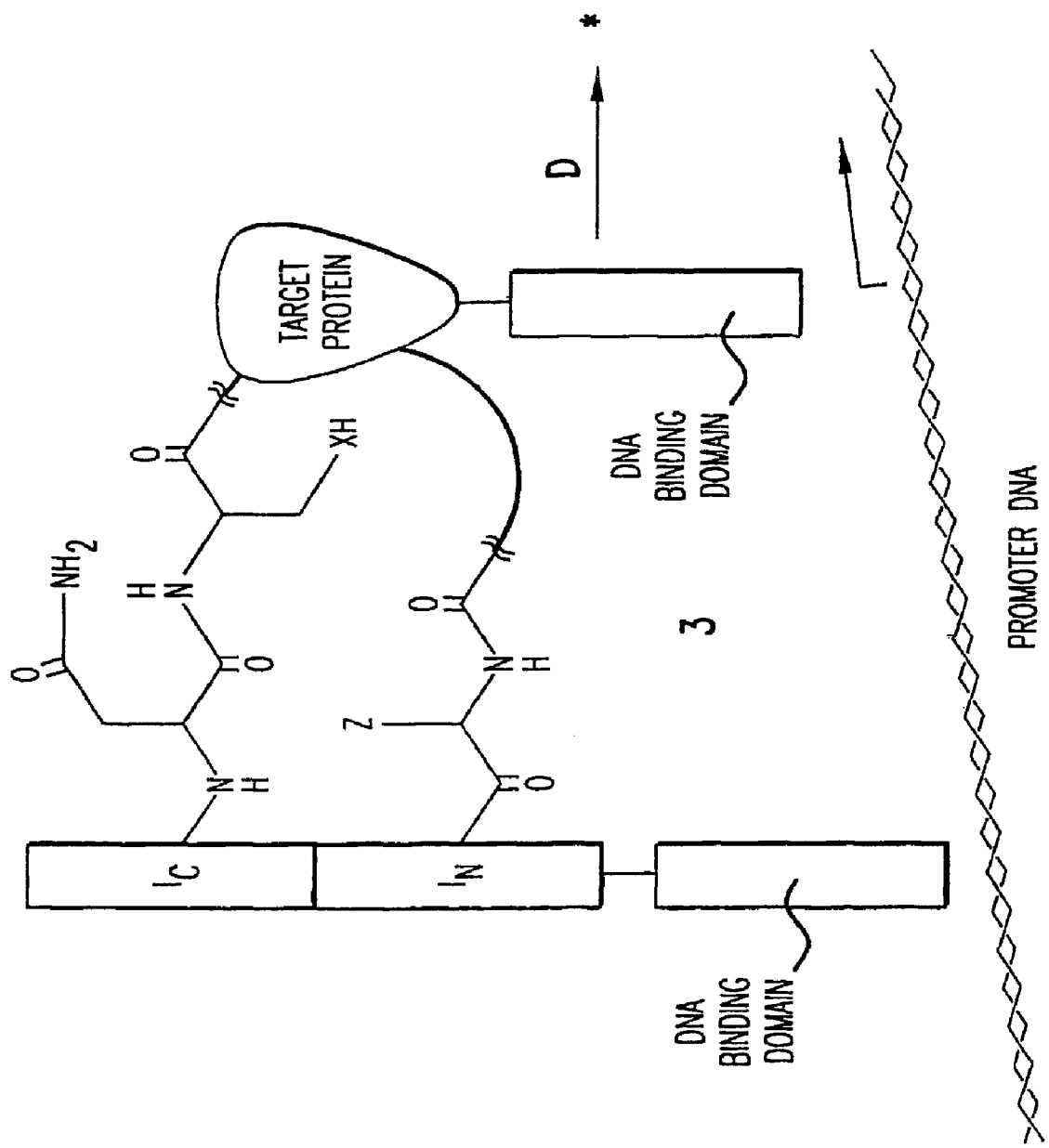

Referring now to FIG. 18, another method for identifying a target protein that interacts with a splicing intermediate is described. In this method, an active intein intermediate (specie 1) is mutagenized to replace the $I_N$ nucleophile (step A) with a non-catalytic amino acid (Z) and to introduce a DNA-binding domain (DBD) downstream of $I_N$ (step B). These processes will inactivate the splicing reaction and will generate an $I_C$-peptide-$I_N$-DBD fusion protein (specie 2). This molecule is then co-expressed with a target protein attached to a DNA-binding domain (step C). Interaction of the fusion protein with the target protein (specie 3) causes activation of a promoter region (step D) leading to expression of the reporter gene (*). This method allows identification of target molecules able to bind the fusion protein. This method can be modified such that a known molecule (in place of an unknown target protein) is attached to a DNA-binding domain, so that fusion proteins displaying a looped peptide that binds the known molecule can be identified.

Figure 19A:
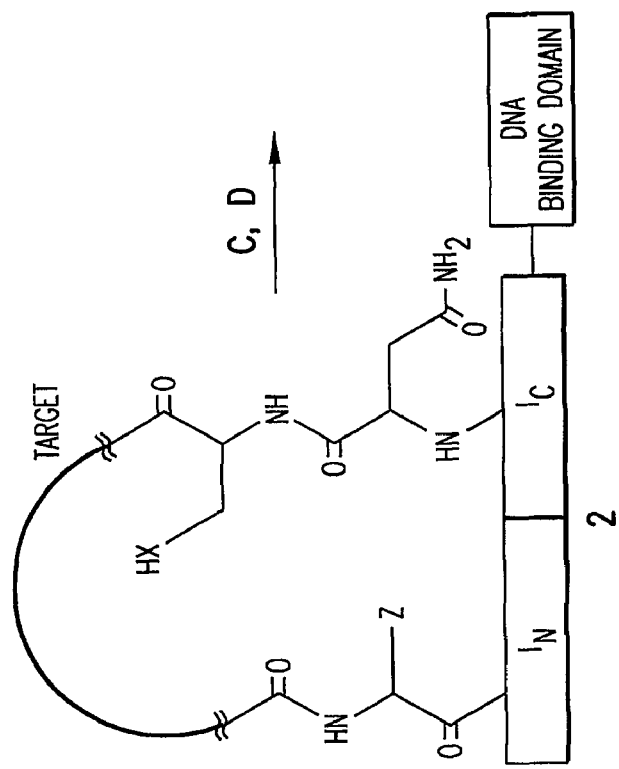
FIG. 19 is a schematic illustration of another method for screening within the invention.
Figure 19A:
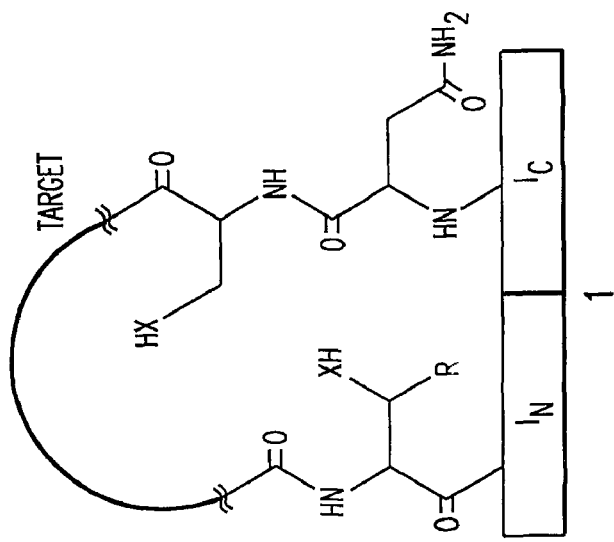
Figure 19B:
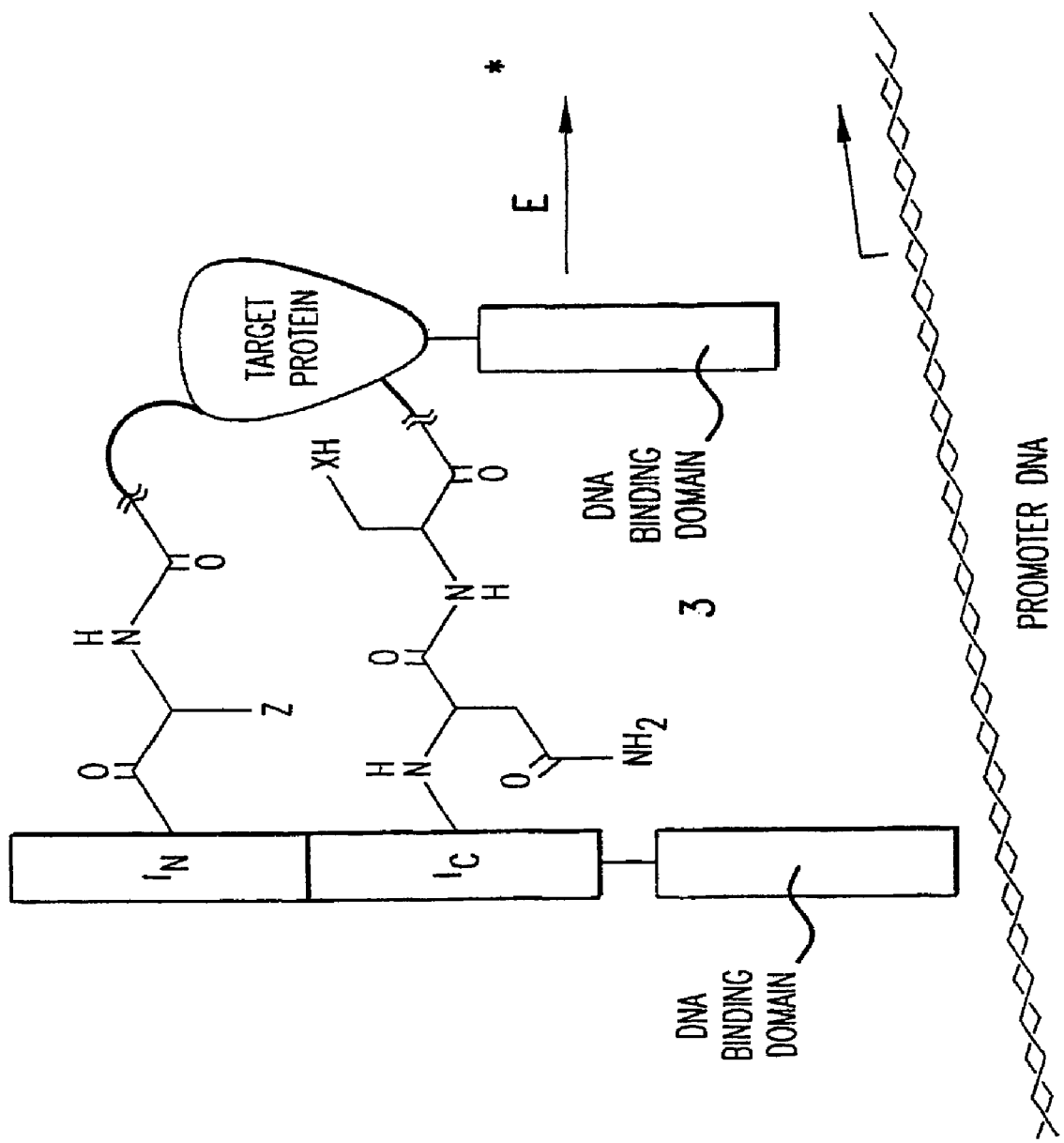

Referring to FIG. 19, yet another method for identifying a target protein that interacts with a splicing intermediate is described. In this method, an active intein intermediate (specie 1) is mutagenized to replace the $I_N$ nucleophile (step A) with a non-catalytic amino acid (Z) and to introduce a DNA-binding domain upstream of $I_C$ (step B). These processes will inactivate the splicing reaction and will generate a DBD-$I_C$-peptide-$I_N$ fusion protein (specie 2). This molecule is then co-expressed with a target protein attached to a DNA-binding domain (step C). Interaction of the fusion protein with the target protein (specie 3) in step D causes activation of a promoter region (step E) leading to expression of the reporter gene (*). This method allows identification of target molecules able to bind the fusion protein. This method can be modified such that a known molecule (in place of an unknown target protein) is attached to a DNA-binding domain, so that fusion proteins displaying a looped peptide that binds the known molecule can be identified.

Targeting Cyclic Peptides and Splicing Intermediates In Vivo

The cyclic peptides and splicing intermediates within the invention can be specifically targeted to particular cellular locales or for extracellular secretion by using modifications of targeting methods known in the art. See, e.g., Wilkinson et al, J. Membrane Biol., 155:189, 1997; Komiya et al, The EMBO J., 17:3886, 1998; Kouranov and Schnell, J. Biol. Chem. 271:31009, 1996; Bhagwat et al, J. Biol. Chem., 274: 24014, 1999; Adam, S. A., Current Opin. Cell Biol. 11:402-406, 1999; Gorlich, D., Current Opin. Cell Biol. 9:412, 1997; Pemberton et al, Current Opin. Cell Biol. 10:292, 1998; Sakaguchi, M., Current Opin. Cell Biol. 8:595, 1997; Folsch et al., The EMBO J. 17:6508, 1998. For example, various signal peptides can be attached to the cyclic peptides or splicing intermediates of the invention to cause them to localize to predetermined cellular compartments or to be secreted into the extracellular space after translation. In this manner, the cyclic peptides or splicing intermediates of the invention can be targeted to cellular locales such as mitochondria, lysosomes, endoplasmic reticula, chloroplasts, golgi, periplasm, the nucleus, the plasma membrane. This method for targeting can also be used in the methods for generating a peptide libraries and methods of screening such libraries where it is desired to identify molecules that interact or exhibit an activity at predetermined cellular locations.

EXAMPLES

Preparation of Cyclic Dihydrofolate Reductase (DHFR) and Cyclic Pseudostellarin F Materials and Methods
Vector Construction The gene for the Ssp DnaE N-intein ($I_N$) was amplified from Ssp 6803 genomic DNA with Taq polymerase and primers introducing 5'-Bglll and NsiI and 3'-PstI restriction sites. The Ssp DnaE $I_C$ gene was amplified similarly with primers introducing 5'-Ncol and 3'-Ndel and SacI restriction sites. Plasmid pDIMCP resulted from individually cloning the intein fragments into pDIMC7 [identical to pDIMC6 (see Ostermeier et al., Proc. Natl. Acad. Sci. USA 96:3562, 1999) except for conversion of a BamHI restriction site into Bglll]. An alanine to histidine mutation in the $I_C$ gene (A35H) was affected by Quick-Change mutagenesis (Stratagene) resulting in pDIMCPAH. Excision of the intein fragments as an NcoI/PstI digest and ligation into pAR4 [derived from pAR3 (Perez-Perez, J. and J. Gutierrez, Gene, 158:141, 1995; American Type Culture Collection (ATCC) #87026) with a unique NcoI in the multiple cloning site] generated pARCP (a in FIG. 3) and pARCPAH. E. coli DHFR was amplified from pET22b-DHFR (Miller, G. P. and S. J. Benkovic, Biochemistry 37:6327, 1998) with primers introducing a 5'-Ndel site followed by $(CAC)_6$ (encoding six histidine residues) and a 3'-PstI site, digested with NdeI/PstI and ligated into NdeI/NsiI digested pARCP or pARCPAH to produce pARCP-DHFR (b in FIG. 3) and pARCPAH-DHFR (c in FIG. 3). A polyhistidine sequence was prepared synthetically with NdeI, NsiI and BspMl sites, and ligated into pARCPAH to produce plasmid pARCP2-6H which encodes cyclo-[CHMHHHHH-HGAGAA]. Plasmid pARCP-p was produced in three steps from pDIMCPAH: (1) Quick-Change mutagenesis introduced an AflII site into $I_N$, generating pDIMCPMA; (2) the pseudostellarin F gene was synthetically prepared and ligated into MfeI/AflII digested pDIMCPMA to produce pDIMCP-p; and (3) the fusion construct was excised from pDIMCP-p as an NcoI/PstI fragment and ligated into NcoI/PstI digested pAR4 to produce pARCP-p (e in FIG. 3). To produce plasmid pARCBD-p, a KpnI site was introduced at the carboxyl terminus of the $I_N$ gene of pARCP-p by Quick-Change mutagenesis to produce pARCPpK. The gene encoding the chitin binding domain was amplified from plasmid pCYBI (New England Biolabs, Inc., Beverly, Mass.) with primers introducing a 5' KpnI site and a 3' HindIII site. Both the PCR product and pARCPpK were digested with KpnI and HindIII and ligated together to generate pARCBD-p (f in FIG. 3). All enzymes were from Promega or New England Biolabs unless otherwise noted.

DHFR Purification

XL I-Blue cells harboring either pARCP-DHFR or pARCPAH-DHFR were grown in LB medium plus 50 ug/ml chloramphenicol at 37° C. until the culture reached an $OD_{600}$ Of 0.7. The culture was induced with L-(+)-arabinose to a final concentration of 0.5% and grown at 28° C. for 24 hours. Cells were harvested by centrifugation (7,000×g, 10 minutes) and frozen in liquid nitrogen. The cells were lysed, and DHFR containing proteins were purified as described (Miller and Benkovic, id). The cyclic product was separated from other DHFR-containing intermediates by FPLC using a Mono-Q column (Amersham Pharmacia) eluted with a gradient of 0-1 M NaCl in 50 mM Tris-HCl over 30 minutes. Western blotting was performed with anti-His (Qiagen) and goat anti-mouse-alkaline phosphatase-conjugated antibodies (Pierce) according to the manufacturers' instructions.

Endoproteinase Lys-C Digestion

Wild-type or cyclic DHFR (50 ug) was treated with 0.5 ug of endoproteinase Lys-C in 0.1 M $NH_4HCO_3$ at 37° C. Samples were taken at 6 and 24 hours, visualized on a SDS/ 16% PAGE gel and submitted for matrix assisted, laser desorption ionization (MALDI) time-of-flight mass spectrometry (Moore, W. T., Methods Enzymol., 289:520, 1997).

DHFR Assays

Thermostability was assayed by preincubation of 100 nM wild type or cyclic DHFR at either 25° C. or 65° C. in MTEN buffer [50 mM 2-(N-morpholino)ethanesulfonic acid (MES), 25 mM tris(hydroxymethyl)aminomethane (Tris), 25 mM ethanolamine and 100 mM NaCl]. Aliquots were taken at various time points and equilibrated to room temperature for five minutes in the presence of 100 uM 7,8-dihydrofolate. Activity assays were initiated with reduced nicotinamide adenine dinucleotide (NADPH) as previously described (Miller and Benkovic, supra).

Synthesis of cyclo-[Ser-Gly-Gly-Tyr-Leu-Pro-Pro-Leu]

To a solution of 3.5 mg (4 umol) of $NH_2$-Ser-Gly-Gly-Tyr-Leu-Pro-Pro-Leu-$CO_2H$ and 1.8 mg (16 umol) of N-hydroxysuccinimide in 20 ml of dimethylformamide was added 3.0 mg (16 umol) of 1-ethyl-3-(3-dimethylaminopropyl)carbodiimide (EDC). The reaction was stirred for 10 hours at 25° C. An additional 3.0 mg of EDC was then added and stirring was continued at 25° C. for another 10 hours. The solvent was removed by rotary evaporation and the residue was dissolved in 2 ml of water for purification by reversed-phase HPLC on a Whatman Partisil 10 ODS-3 9.4-mM×50-cm column eluted with a linear gradient of 0-50% (vol/vol) acetonitrile in 0.1% trifluoroacetic acid/water over 30 minutes. The appropriate fractions were lyophilized to yield 2.8 mg (80%) of a white solid, [m/z 785 ($MH^+$)]. $^1$H-NMR and UV-visible spectra of the synthetically prepared material were consistent with published spectra for the isolated natural product (Morita, H., et al, Tetrahedron 50:9975, 1994).

Pseudostellarin F Purification

E. coli strains XL1-Blue, DH5a or BL21-DE3 harboring pARCP-p were grown and harvested as described for DHFR purification. The media (500 ml) was extracted three times with 1-butanol (3×100 ml). The extracts were combined and evaporated, and the solid residue was resuspended in 2 ml 0.1 M $K_2HPO_4$ (pH 8.0; lysis buffer). Cells were resuspended in 10 ml of lysis buffer, sonicated, and clarified by centrifugation (20,000×g, 20 minutes). The lysate was extracted (3×5 ml of n-butanol), and extracts were combined, evaporated and resuspended in 500 ul of lysis buffer. The recombinant product was purified from lysate and media extracts by HPLC as described above. Lyophilization of the appropriate fractions from the lysate and media extractions yielded an oily residue, m/z 785.47 ($MH^+$), 807.43 ($MNa^+$) and 823.44 ($MK^+$). $^1$H-NMR and UV-visible spectra of the recombinant material were consistent with published spectra for the isolated natural product (Morita et al, supra). Proteins fused to the chitin binding domain were prepared as described above through generation of the clarified lysate. The lysate was passed over a chitin column (New England Biolabs, Inc.) equilibrated with lysis buffer. The column was eluted isocratically, and fractions containing splicing intermediates were pooled and submitted for MALDI mass spectral analysis.

Tyrosinase Cloning

The tyrosinase gene (including ORF 438) from *Streptomyces antibioticus* (Berman et al, Gene 37:101, 1985) was amplified with Vent-polymerase from pIJ702 (ATCC no. 35287) with primers introducing 5'

NdeI and 3' EcoRI restriction sites. The PCR product was digested with NdeI and EcoRI and ligated into similarly digested pDIMN2 (Ostermeier et al, supra) to generate pDIMN-Y. Transformed ligation mixtures were grown at ambient temperature for 5 days, and colonies that expressed tyrosinase were identified by pigment formation on FeCuY plates [LB agar plates containing ampicillin (200 ug/ml), $FeCl_3.6H_2O$ (0.2 mM), $CuSO_4.5H_2O$ (0.2 mM), L-tyrosine (0.3 mg/ml, Y) and isopropyl-B-D-galactoside (1 mM)] (Della-Cioppa, G. et al., Biotechnology 8:634, 1990).

Results

Design of Genetic Constructs

The genes encoding Ssp $I_C$ and $I_N$ were amplified from Ssp genomic DNA by standard molecular biology methods (Sambrook, et al, supra) and serially ligated into pDIMC7. The resulting cyclization precursor (CP) fragment was excised from pDIMC7 and cloned adjacent to the AraB promoter of pAR3 to generate the pARCP vector series (FIG. 3). These vectors activate the expression of cyclization precursors in the presence of arabinose. The E. coli DHFR gene was cloned between the NdeI and NsiI sites of pARCP to create an in frame fusion with each of the split intein genes (b and c in FIG. 3). The PCR primer used to amplify DHFR also introduced a sequence encoding a six-histidine tag at the 5' end of the DHFR gene to allow immunodetection of the region to be cyclized. Two DHFR constructs were assembled in order to investigate the role of the penultimate residue of $I_C$ in acid/base catalysis of asparagine side chain cyclization. Plasmid pARCP-DHFR (b in FIG. 3) encodes wild type $I_C$, which has an alanine residue neighboring the terminal asparagine. Plasmid pARCPAH-DHFR (c in FIG. 3) incorporates an alanine-to-histidine mutation at the penultimate position in $I_C$ gene. To produce pseudostellarin F (cyclo-[SGGYLPPL]), the vector was modified by silent mutation to create an AflII site at the 5'-end of the $I_N$ gene (d in FIG. 3). An MfeI site occurs naturally at the 3'-end of the wild-type $I_C$ gene. Ligation of a synthetically prepared, double-stranded insert encoding pseudostellarin F into the modified vector produced plasmid pARCP-p (e in FIG. 3). A KpnI site was introduced at the 3'-end of the $I_N$ gene in order to fuse the gene for the chitin-binding domain to the pseudostellarin-producing construct (f in FIG. 3).

Production and Characterization of Cyclic DHFR

Figure 4:
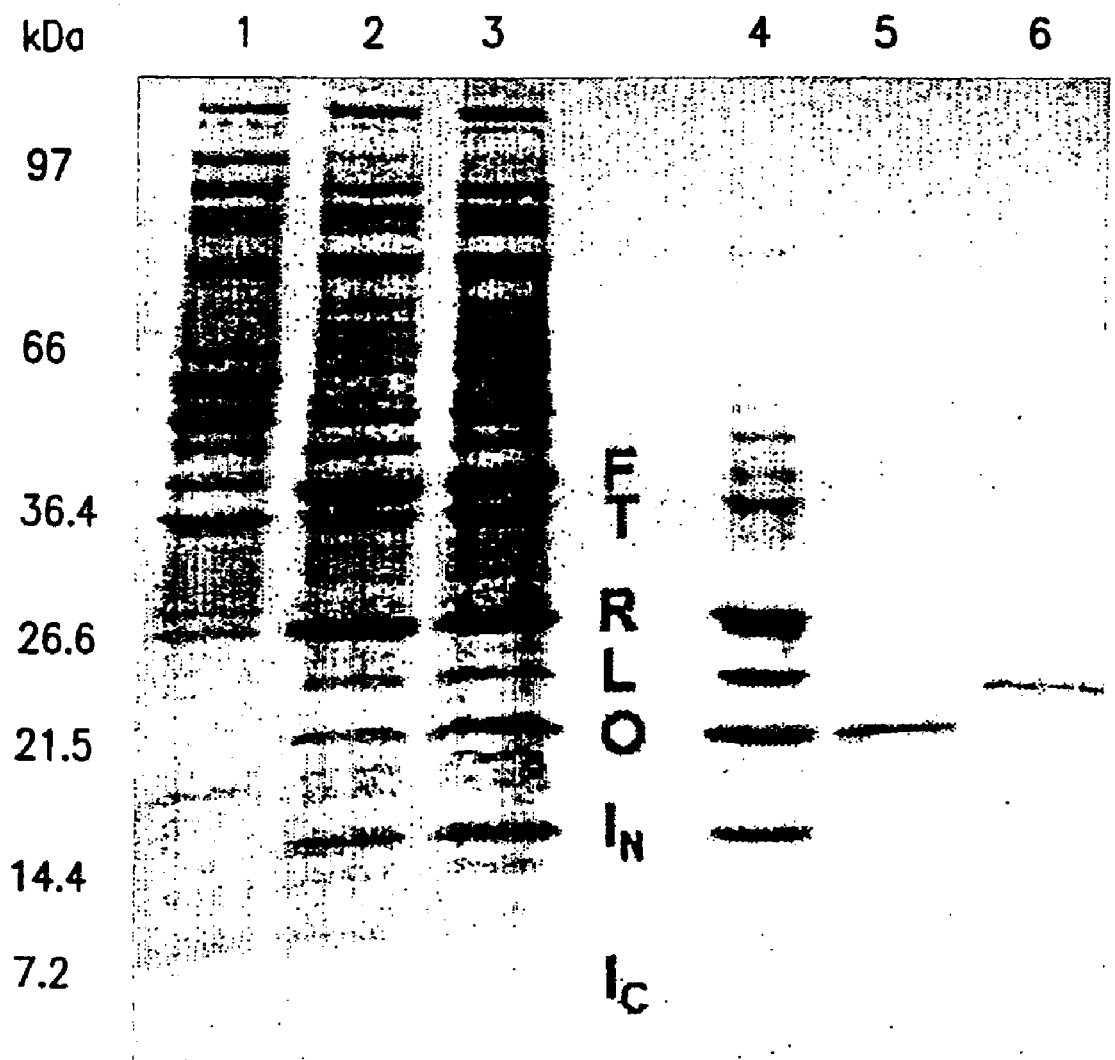
FIG. 4 is a photograph of a sodium dodecylsulfate polyacrylamide gel electrophoresis (SDS-PAGE) analysis of dihydrofolate reductase (DHFR) cyclization on a 10-20% gradient, Tris/glycine ready-gel (Biorad).

DHFR cyclization was readily apparent by SDS-PAGE upon arabinose induction of pARCP-DHFR as shown in FIG. 4 (F: $I_C$-DHFR-$I_N$ fusion protein. T: $I_C$-DHFR-$I_N$ fusion thioester intermediate. R: $I_C$-DHFR lariat intermediate. L: linear DHFR. 0: cyclic DHFR. $I_N$: N-intein. $I_C$: C-intein. Lane 1: uninduced XL1-Blue/pARCP-DHFR. Lane 2: arabinose induced XLI-Blue/pARCP-DHFR. Lane 3: arabinose induced XLIBlue/pARCPAH-DHFR. Lane 4: lane 3 crude lysate after methotrexate agarose. Lane 5: lane 4 material post FPLC. Lane 6: Wild-type DHFR).

Bands with apparent molecular weights corresponding to the linear (L, 23 kDa) and cyclic (0, 21 kDa) DHFR products, the fusion protein (F, 37 kDa), $I_N$ (14 kDa) and $I_C$ (4 kDa) were clearly visible, as were bands tentatively assigned as the thioester (T, 36 kDa) and lariat intermediates (R, 26 kDa) (FIG. 4, lane 2). Mutation of the penultimate residue of $I_C$ (A35) from alanine to histidine (c in FIG. 3) improved the yield of cyclic DHFR (FIG. 4, lane 3). Methotrexate-agarose affinity chromatography of the crude lysate (FIG. 4, lane 4) confirmed that the majority of the induced bands contained correctly folded DHFR. Although $I_N$ is not covalently attached to DHFR, it was retained on the methotrexate column presumably due to non-covalent complex formation with the $I_C$-DHFR lariat intermediate (R). The methotrexate-agarose eluant was fractionated by FPLC, allowing purification of 5 mg of the cyclic product per liter of culture (FIG. 4, lane 5). Western blotting (not shown) with an anti-His antibody demonstrated the presence of the polyhistidine linker sequence (d in FIG. 3) in the FPLC-purified protein. The protein migrated more rapidly in SDS/PAGE analyses than recombinant DHFR (FIG. 4, lane 6) despite the extra 11-amino acid linker sequence (b in FIG. 3) implying an additional topological constraint. Furthermore, no reaction was detected when the FPLC-purified protein was reacted with phenylisothiocyanate (Edman, P., Acta Chem. Scand., 4:283, 1950), suggesting that the amino terminus was unavailable.

Figure 5:
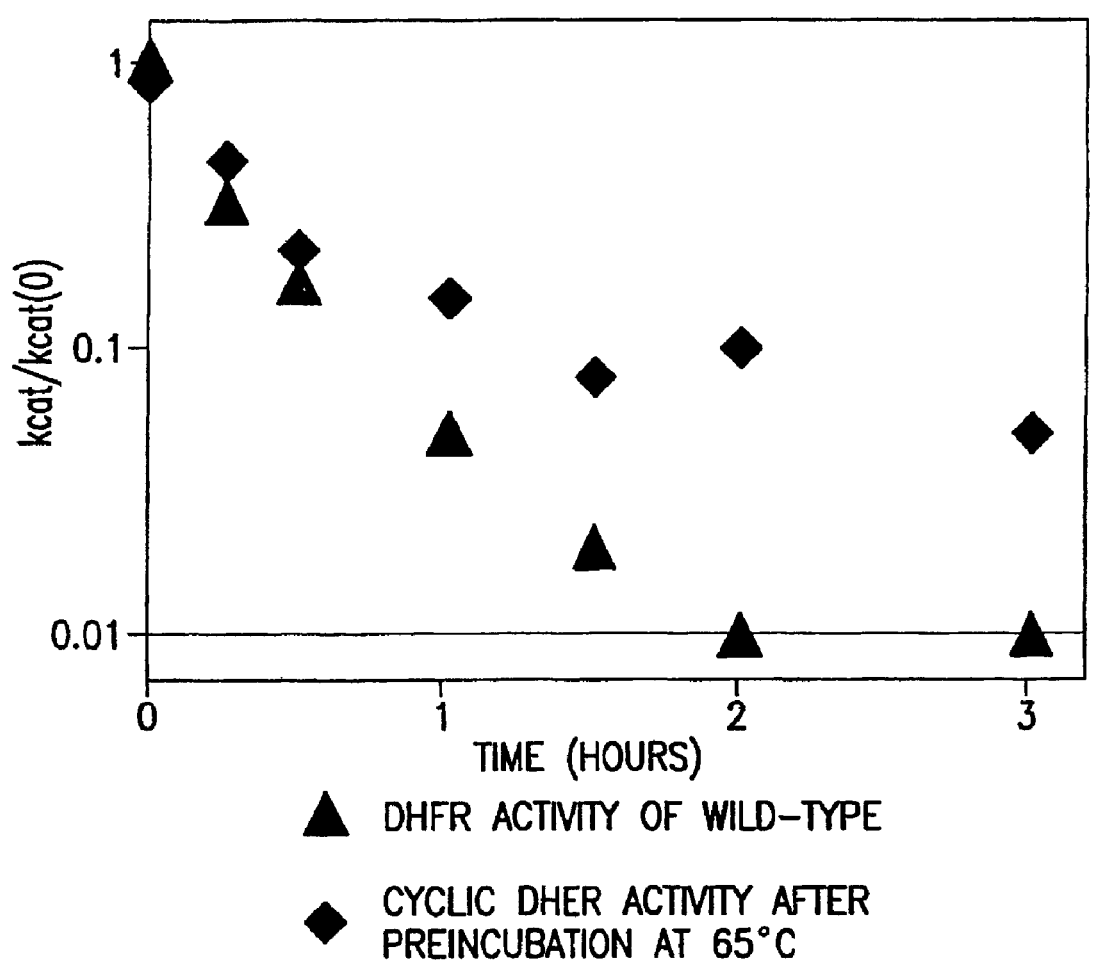
FIG. 5 is a graph of DHFR activity of wild-type (triangles) and cyclic DHFR (diamonds) activity after preincubation at 65° C.
Figure 6:
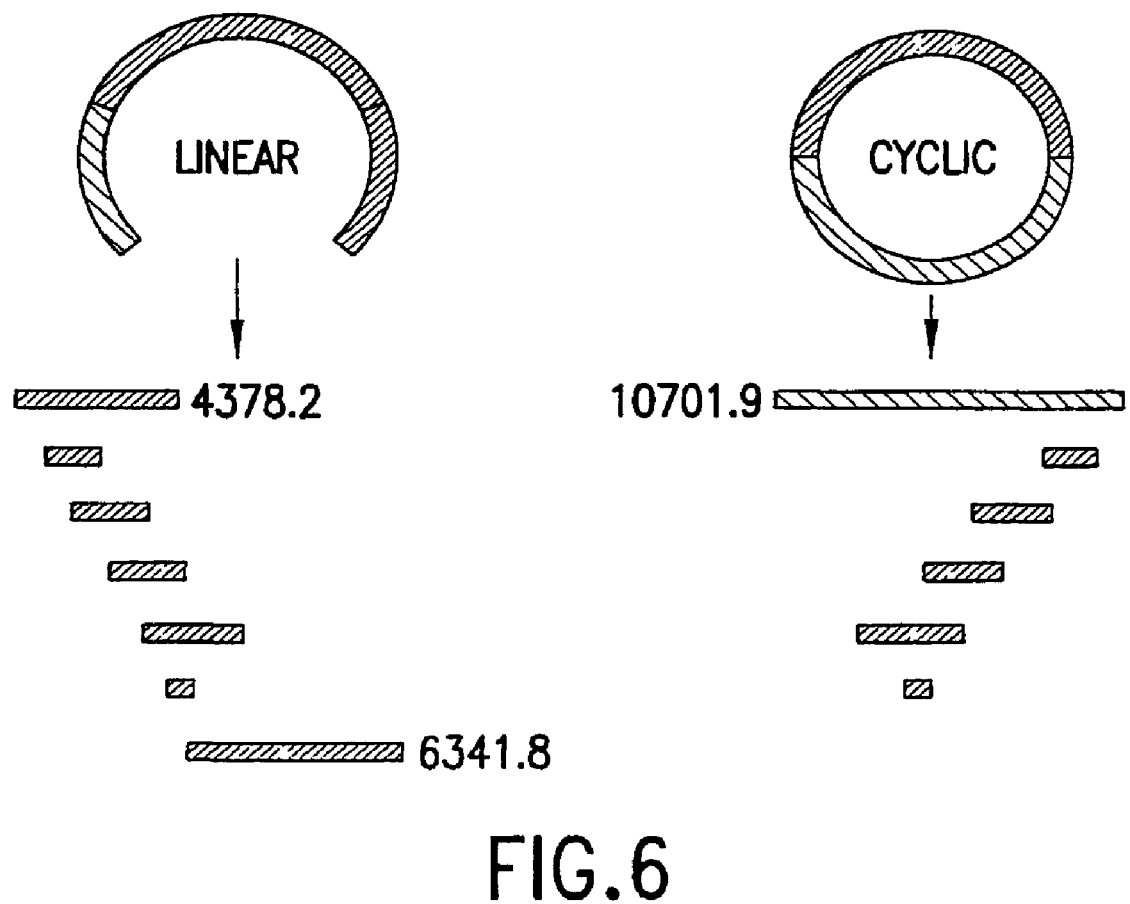
FIG. 6 is a schematic illustration of the expected endoproteinase Lys-C digestion pattern for linear and cyclic DHFR.
Figure 7A:
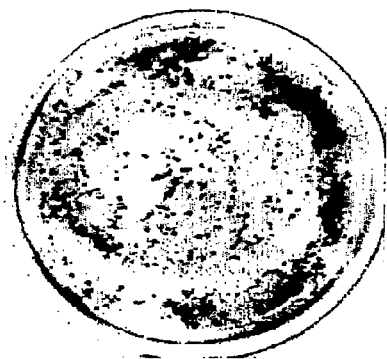
FIG. 7 is a photograph of FeCuY plates used in an in vivo assay to detect tyrosinase inhibition by pseudostellarin F.
Figure 7B:
Figure 7C:
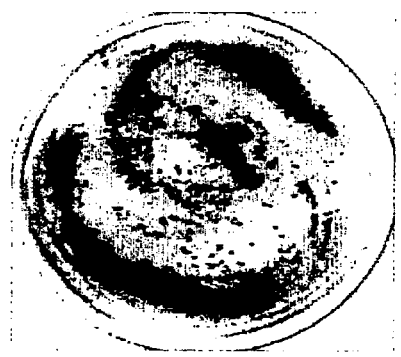
Figure 7D:
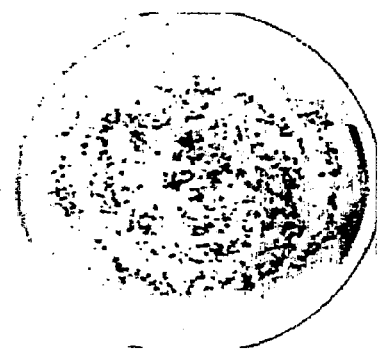

Cyclic DHFR had steady-state kinetic parameters and substrate, cofactor and methotrexate dissociation constants which were indistinguishable from the wild type enzyme at 25° C. Activity assays conducted after 65° C. preincubation of wild type and cyclic DHFR indicated that cyclization improved the thermostability of the enzyme (FIG. 5). Endoproteinase Lys-C digestion was used to demonstrate unambiguously that the FPLC purified protein was cyclic DHFR. Digestion of the wild type enzyme produces amino-terminal (4.4 kDa) and carboxy-terminal (6.3 kDa) fragments; in a cyclic protein, these two fragments would be joined, resulting in a 10.7 kDa digestion product (FIG. 6). The FPLC purified material was resistant to proteolysis compared to the wild type enzyme, and mass spectral analysis of the digestion mixtures identified a 10.7 kDa peak in the product resulting from the cyclic protein, which was absent in the wild type enzyme (data not shown).

Production and Characterization of Pseudostellarin F

Pseudostellarin F production was readily detected in vivo through inhibition of recombinant *Streptomyces antibioticus* tyrosinase (FIG. 7). In the experiment shown in FIG. 7, XLI-Blue cells were co-transformed with pDIM-NY and either pARCP2-6H (a & b) or pARCP-p (c & d). The cells were plated on FeCuY plates with chloramphenicol (50 ug/ml), either without (a & c) or with (b & d) L-(+)arabinose (0.5%).

Co-expression of pseudostellarin F in tyrosinase expressing cells dramatically reduced pigment formation (d in FIG. 7). Expression of an unrelated cyclic peptide from pARCP2-6H failed to inhibit tyrosinase (a and b in FIG. 7), and inhibition absolutely required arabinose induction (compare c and d in FIG. 7). SDS/PAGE analysis of arabinose-induced pARCP-p in several bacterial strains (BL21-DE3, DH5a, and XLI-Blue) allowed the visualization of bands corresponding to the fusion protein (F), thioester intermediate (T) and $I_N$. An intense, low molecular weight band was also visible, but the resolution was insufficient to separate the lariat intermediate (R) and $I_C$ (data not shown). Although pseudostellarin F was too small to be visualized by SDS/PAGE, mass spectral analysis indicated its presence in both the crude cell lysate and media. Approximately 30 ug of the recombinant cyclic peptide was isolated from the cell lysate per gram of wet cell mass. Pseudostellarin F was also isolated from the media by 1-butanol extraction followed by HPLC with a yield that varied between 2 mg/liter (XLI Blue) and 20 mg/liter (BL21-DE3) depending on the expression strain. The NMR spectrum of the recombinant material was consistent with that reported for the natural product (Morita et al., supra), and the retention time of the bacterially expressed cyclic peptide was identical to a synthetically prepared standard. The recombinant material failed to react with ninhydrin (see, Gordon, A. J., and R. A. Ford, The Chemist's Companion: A Handbook of Practical Data, Techniques, and References, Wiley Interscience, New York, 1972), indicating a backbone cyclic peptide (lactam) rather than a lactone product. Neither HPLC nor mass spectral analysis provided any evidence for production of the linear parent peptide.

A chitin-binding domain was fused to the carboxy-terminus of $I_N$ to affinity-purify intermediates of the intein-mediated ligation reaction and characterize them by MALDI mass spectrometry (Table 1).

TABLE 1

Mass spectral characterization of pseudostellarin F cyclization intermediates

| Reaction Component | Mass, Da | | |
|---|---|---|---|
| | Linear | Cyclic | Observed |
| F, T | 24,380.5 | NA | 24,380.4 |
| $1_N$ | 19,642.0 | NA | 19,642.3 |
| R | 4,756.5 | 4,738.5 | 4,756.2 |
| $I_c$ | 3,969.2 | 3,951.2 | 3,953.0 |
| Pseudostellarin F | 802.4 | 784.4 | 784.4 |

All of the intermediates of the splicing reaction, including $I_C$, were retained when the crude cell lysate from arabinose-induced pARCBD-p in XL1-Blue was passed over a chitin affinity column. Pseudostellarin F was recovered from the unretained material by 1-butanol extraction. The observed molecular masses for the fusion protein (F), the thioester intermediate (T) and $I_N$ were in excellent agreement with the values predicted from the gene sequence. The mass of $I_C$ was consistent with the asparagine-cyclized form as predicted from the proposed mechanism of product release. The molecular mass of the lariat intermediate (R) was more consistent with the linear $I_C$-pseudostellarin F fusion product than the branched lactone product expected from the transesterification reaction.

Other Embodiments

While the above specification contains many specifics, these should not be construed as limitations on the scope of the invention, but rather as examples of preferred embodiments thereof. Many other variations are possible. Accordingly, the scope of the invention should be determined not by the embodiments illustrated, but by the appended claims and their legal equivalents.

What is claimed is:

1. An isolated cell comprising a polypeptide comprising a carboxy-terminal portion of a split intein (C-intein), an amino-terminal portion of a split intein (N-intein), and a target peptide flanked on one end with the carboxy-terminal portion of a split intein (C-intein) and on its other end with the amino-terminal portion of a split intein (N-intein), wherein the polypeptide is selected from the group consisting of: (a) a polypeptide that spontaneously splices in the host system to yield a cyclized form of the target peptide, and (b) a splicing intermediate of a cyclized form of the target peptide.

2. The isolated cell of claim 1, wherein the polypeptide is a polypeptide that spontaneously splices in the host system to yield a cyclized form of the target peptide.

3. The isolated cell of claim 1, wherein the polypeptide is a splicing intermediate of a cyclized form of the target peptide.

4. The isolated cell of claim 1, wherein the target peptide has a first end fused to the carboxy-terminal portion of a split intein (C-intein) and a second end fused to the amino-terminal portion of a split intein (N-intein).

5. The isolated cell of claim 1, wherein both the carboxy-terminal portion of a split intein (C-intein) and the amino-terminal portion of a split intein (N-intein) are naturally-occurring split inteins.

6. The isolated cell of claim 5, wherein both the carboxy-terminal portion of a split intein (C-intein) and the amino-terminal portion of a split intein (N-intein) are Ssp DnaE.

7. The isolated cell of claim 1, wherein at least one of the carboxy-terminal portion of a split intein (C-intein) and the amino-terminal portion of a split intein (N-intein) is a non-naturally occurring split intein.

8. The isolated cell of claim 7, wherein the non-naturally occurring split intein is selected from the group consisting of RecA, DnaB, Psp Pol-I, and Pfu inteins.

9. The isolated cell of claim 1, wherein both the carboxy terminal portion of a split intein and the amino terminal portion of a split intein are non-naturally occurring split inteins.

10. The isolated cell of claim 3, wherein the splicing intermediate is a active intein intermediate.

11. The isolated cell of claim 3, wherein the splicing intermediate is a thioester intermediate.

12. The isolated cell of claim 3, wherein the splicing intermediate is a lariat intermediate.

* * * * *